(12) United States Patent
Edwards et al.

(10) Patent No.: US 8,926,594 B2
(45) Date of Patent: Jan. 6, 2015

(54) DEVICES, SYSTEMS AND METHODS FOR MEDICAMENT DELIVERY

(75) Inventors: Eric Shawn Edwards, Midlothian, VA (US); Evan Thomas Edwards, Fredericksburg, VA (US); Mark J. Licata, Doswell, VA (US); Paul F. Meyers, Fishers, IN (US); David A. Weinzierl, Andover, MN (US)

(73) Assignee: kaleo, Inc., Richmond, VA (US)

( * ) Notice: Subject to any disclaimer, the term of this patent is extended or adjusted under 35 U.S.C. 154(b) by 58 days.

(21) Appl. No.: 13/404,699

(22) Filed: Feb. 24, 2012

(65) Prior Publication Data

US 2012/0226226 A1 Sep. 6, 2012

Related U.S. Application Data

(63) Continuation of application No. 12/794,020, filed on Jun. 4, 2010, now Pat. No. 8,206,360, which is a (Continued)

(51) Int. Cl.
| | | |
|---|---|---|
| *A61K 9/22* | (2006.01) | |
| *A61M 5/20* | (2006.01) | |
| *A61M 5/142* | (2006.01) | |
| *A61M 5/19* | (2006.01) | |
| *A61M 5/31* | (2006.01) | |
| *A61M 5/32* | (2006.01) | |
| *A61M 15/00* | (2006.01) | |

(52) U.S. Cl.
CPC ......... *A61M 5/2033* (2013.01); *A61M 5/14244* (2013.01); *A61M 5/19* (2013.01); *A61M 5/2053* (2013.01); *A61M 5/3129* (2013.01); *A61M 5/326* (2013.01); *A61M 5/3287* (2013.01); *A61M 15/009* (2013.01); *A61M 2005/206* (2013.01); *A61M 2005/2073* (2013.01); *A61M 2205/50* (2013.01); *A61M 2205/581* (2013.01); *A61M 2205/582* (2013.01); *A61M 2205/583* (2013.01); *A61M 2205/8206* (2013.01); *A61M 5/3204* (2013.01)
USPC .......... 604/890.1; 604/134; 604/137

(58) Field of Classification Search
CPC .......................... A61M 2205/581; A61M 5/20
USPC ......... 604/131, 134–137; 128/200.14, 200.23
See application file for complete search history.

(56) References Cited

U.S. PATENT DOCUMENTS

| 2,960,087 A | 11/1960 | Uytenbogaart |
|---|---|---|
| 3,055,362 A | 9/1962 | Uytenbogaart |

(Continued)

FOREIGN PATENT DOCUMENTS

| EP | 1043037 A2 | 10/2000 |
|---|---|---|
| EP | 1287840 A1 | 5/2003 |

(Continued)

OTHER PUBLICATIONS

English Translation of Office Action for Japanese Patent Application No. 2009-502964, mailed May 17, 2012.

(Continued)

*Primary Examiner* — Emily Schmidt
(74) *Attorney, Agent, or Firm* — Cooley LLP

(57) ABSTRACT

An apparatus includes a label configured to be coupled to a medicament delivery device. The label includes a first surface and a second surface. The first surface is configured to be coupled to an outer surface of the medicament delivery device. The second surface includes a textual indicia. The label further includes an electronic circuit system configured to output an electronic signal.

31 Claims, 27 Drawing Sheets

Related U.S. Application Data continuation of application No. 11/621,236, filed on Jan. 9, 2007, now Pat. No. 7,731,686, which is a continuation-in-part of application No. 10/572,148, filed as application No. PCT/US2006/003415 on Feb. 1, 2006, now Pat. No. 7,749,194.

(60) Provisional application No. 60/648,822, filed on Feb. 1, 2005, provisional application No. 60/731,886, filed on Oct. 31, 2005, provisional application No. 60/787,046, filed on Mar. 29, 2006.

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,124,024 A | 11/1978 | Schwebel et al. |
| 4,149,394 A | 4/1979 | Sornes |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,381 A | 10/1989 | Vetter |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,417,660 A | 5/1995 | Martin |
| 5,466,217 A | 11/1995 | Myers et al. |
| 5,505,192 A | 4/1996 | Samiotes et al. |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,610,992 A | 3/1997 | Hickman |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,002,781 A | 12/1999 | Takayama et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |

(56) References Cited

U.S. PATENT DOCUMENTS

| | | |
|---|---|---|
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 * | 6/2001 | Nicholson et al. ............ 700/241 |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,285,757 B1 | 9/2001 | Carroll et al. |
| 6,312,412 B1 | 11/2001 | Saied et al. |
| 6,317,630 B1 | 11/2001 | Gross et al. |
| 6,321,654 B1 | 11/2001 | Robinson |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Dailey et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,597,794 B2 | 7/2003 | Cole et al. |
| 6,633,796 B1 | 10/2003 | Pool et al. |
| 6,641,566 B2 | 11/2003 | Douglas et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,963,280 B2 | 11/2005 | Eskildsen |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,093,595 B2 | 8/2006 | Nesbitt |
| 7,113,101 B2 | 9/2006 | Peterson et al. |
| 7,116,233 B2 | 10/2006 | Zhurin |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,871,393 B2 | 1/2011 | Monroe |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,149,111 B2 | 4/2012 | Monroe |
| 8,212,658 B2 | 7/2012 | Monroe |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 2001/0005781 A1 | 6/2001 | Bergens et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120212 A1 | 6/2003 | Dedig et al. |
| 2003/0130853 A1 | 7/2003 | Maire |
| 2003/0132128 A1 | 7/2003 | Mazur |

(56) References Cited

U.S. PATENT DOCUMENTS

| | | |
|---|---|---|
| 2003/0135388 A1 | 7/2003 | Martucci et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0069667 A1 | 4/2004 | Tomellini et al. |
| 2004/0078001 A1 | 4/2004 | Langley et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0186221 A1 | 8/2005 | Reynolds et al. |
| 2005/0197654 A1 | 9/2005 | Edman et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129708 A1 | 6/2007 | Edwards et al. |
| 2007/0184847 A1 | 8/2007 | Hansen et al. |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0260210 A1 | 11/2007 | Conroy |
| 2008/0059133 A1 | 3/2008 | Edwards et al. |
| 2008/0103490 A1 | 5/2008 | Edwards et al. |
| 2008/0111685 A1 | 5/2008 | Olson et al. |
| 2008/0160492 A1 | 7/2008 | Campbell et al. |
| 2008/0230057 A1 | 9/2008 | Sutherland |
| 2008/0269689 A1 | 10/2008 | Edwards et al. |
| 2009/0024112 A1 | 1/2009 | Edwards et al. |
| 2009/0030285 A1 | 1/2009 | Andersen |
| 2009/0062728 A1 | 3/2009 | Woo |
| 2009/0143761 A1 | 6/2009 | Cantor et al. |
| 2009/0194104 A1 | 8/2009 | Van Sickle |
| 2009/0240200 A1 | 9/2009 | Heneveld et al. |
| 2010/0160894 A1 | 6/2010 | Julian et al. |
| 2010/0192948 A1 | 8/2010 | Sutherland et al. |
| 2010/0211005 A1 | 8/2010 | Edwards et al. |
| 2010/0250280 A1 | 9/2010 | Sutherland |
| 2010/0309012 A1 | 12/2010 | Edwards et al. |
| 2010/0318035 A1 | 12/2010 | Edwards et al. |
| 2011/0144574 A1 | 6/2011 | Kamen et al. |
| 2011/0295215 A1 | 12/2011 | Nielsen et al. |
| 2012/0008811 A1 | 1/2012 | Edwards et al. |
| 2012/0071819 A1 | 3/2012 | Bruggemann et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2013/0184649 A1 | 7/2013 | Edwards et al. |
| 2013/0266919 A1 | 10/2013 | Baker et al. |
| 2013/0280687 A1 | 10/2013 | Edwards et al. |
| 2013/0323699 A1 | 12/2013 | Edwards et al. |

FOREIGN PATENT DOCUMENTS

| | | |
|---|---|---|
| EP | 1462134 A1 | 9/2004 |
| EP | 1 518 575 A1 | 3/2005 |
| EP | 1712178 A2 | 10/2006 |
| JP | 2006-034845 | 2/2006 |
| MX | PA04009276 | 1/2005 |
| WO | WO 91/04760 A1 | 4/1991 |
| WO | WO93/02720 | 2/1993 |
| WO | WO 95/26009 | 9/1995 |
| WO | WO 96/25965 | 8/1996 |
| WO | WO 97/30742 | 8/1997 |
| WO | WO 99/07425 | 2/1999 |
| WO | WO 99/43283 | 9/1999 |
| WO | WO 01/24690 A2 | 4/2001 |
| WO | WO 01/26020 A1 | 4/2001 |
| WO | WO 01/41849 A3 | 6/2001 |
| WO | WO 01/88828 | 11/2001 |
| WO | WO 01/93926 A2 | 12/2001 |
| WO | WO 02/24257 A1 | 3/2002 |
| WO | WO 02/051471 A1 | 7/2002 |
| WO | WO 03/057283 A1 | 7/2003 |
| WO | WO 03/095001 A1 | 11/2003 |
| WO | WO 03/097133 A1 | 11/2003 |
| WO | WO 2004/041330 A2 | 5/2004 |
| WO | WO 2005/050526 A2 | 6/2005 |
| WO | WO 2005/077441 A2 | 8/2005 |
| WO | WO 2006/045525 A1 | 5/2006 |
| WO | WO 2006/083876 A2 | 8/2006 |
| WO | WO 2006/085175 A1 | 8/2006 |
| WO | WO 2006/085204 A1 | 8/2006 |
| WO | WO 2006/109778 A1 | 10/2006 |
| WO | WO 2006/123956 A1 | 11/2006 |
| WO | WO2006/125692 | 11/2006 |
| WO | WO 2007/083115 | 7/2007 |
| WO | WO 2007/088444 A1 | 8/2007 |
| WO | WO 2008/005315 | 1/2008 |
| WO | WO 2008/148864 | 12/2008 |
| WO | WO 2010/114392 A1 | 10/2010 |
| WO | WO 2013/043063 A1 | 3/2013 |
| WO | WO 2013/044172 A1 | 3/2013 |

OTHER PUBLICATIONS

EnglishTranslation of Office Action for Chinese Patent Application No. 200780011264.5, mailed Mar. 28, 2013.

Non-Final Office Action for U.S. Appl. No. 13/962,336, mailed Nov. 20, 2013.

"Solutions for Medical Devices," 3M Brochure, © 3M 2006 80-6201-3490-0.

Merle Tingelstad, "Revolutionary Medical Technology Increases Demand for Flexible Interconnects," [online] May 15, 2006 [retrieved on Nov. 15, 2006] Retrieved from the Internet <URL:http://www.ecnmag.com/index.asp?layout=articlePrint &ArticleID=CA6332947 >.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >.

"Flexible circuits capabilities of Flexible Technology Limited," Our Flexible Circuits Capabilities [online] [retrieved on Aug. 28, 2006]

(56) References Cited

OTHER PUBLICATIONS

Retrieved from the Internet <URL: http://www.flexibletechnology.com/Flexible circuits Capability.htm >.
"Flex Circuits/flexible circuits design guide," [online] [retrieved on Aug. 28, 2006] Retrieved from the Internet <URL: http://flexiblecircuit.co.uk/Flex Circuits Design Guide.htm >.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp >.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >.
Roger Allan, "Medical Electronics: Technology Advances Will Revolutionize Healthcare," Sep. 30, 2002 [online] [retrieved on Nov. 28, 2006] Retrieved from the Internet <URL:http://www.elecdesign.com/Articles/Index.cfm?AD=1&ArticleID=2041>.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.
Dr. Oliver Scholz, "Drug depot in a tooth," [online] [retrieved on Feb. 6, 2007] Retrieved from the Internet <URL:http://www.fraunhofer.de/fhg/EN/press/pi/2007/02Mediendienst22007Thema2.jsp?print=true.
Heartsine Technology, samaritan™ Pad Accessories [online] [retrieved on Jun. 1, 2007] Retrieved from the Internet <URL: http://www.heartsine.com/aboutsam-accessories.htm>.
CliniSense Corporation, "Drug delivery devices A potentially harsh environment for drugs," Stability [online] [retrieved on Jun. 1, 2007] Retrieved from the Internet <URL: http://www.clinisense.com/devices.htm>.
CliniSense Corporation, "LifeTrack Technology A new method to detect improper storage." Stability [online] [retrieved on Jun. 1, 2007] Retrieved from the Internet <URL: http://www.clinisense.com/tech.htm>.
AED Professionals™ Brochure [online] [retrieved on Jun. 1, 2007] Retrieved from the Internet <URL: http://www.aedprofessionals.com/>.
Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL:http://www.drugdeliverytech-online.com/drugdelivery/200702/templates/pageviewer_print?pg=44&pm=8 >.
Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamel_trainer.html/>.
Laura Lin Gosbee, "Nuts! I Can't Figure Out How to Use My Life-Saving Epinephrine Auto-Injector," Joint Commision Journal on Quality and Safety, vol. 30, No. 4, Apr. 2004.
Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>.
Search Report and Written Opinion for International Patent Application No. PCT/US06/03415 mailed Jul. 13, 2006, 10 pages.
Search Report and Written Opinion for International Patent Application No. PCT/US07/007626 mailed Sep. 29, 2008.
Combined Search and Examination Report for GB 0818178.6, mailed Dec. 1, 2008.
Office Action for U.S. Appl. No. 11/621,236, mailed Feb. 3, 2009.
Examination Report for British Patent Application No. GB 0822532.8, mailed May 21, 2009.
Examination Report for British Patent Application No. GB 0818178.6, mailed Mar. 23, 2009.
Examination Report for British Patent Application No. GB 0905194.7, mailed May 8, 2009.
Office Action for U.S. Appl. No. 10/572,148, mailed Jun. 19, 2009.
Final Office Action for U.S. Appl. No. 11/621,236, mailed Jul. 1, 2009.
Examination Report for British Patent Application No. GB 0818178.6, mailed Jul. 9, 2009.
Office Action for U.S. Appl. No. 11/621,236, mailed Jan. 11, 2010.
Final Office Action for U.S. Appl. No. 10/572,148, mailed Feb. 3, 2010.
Search Report and Written Opinion for International Patent Application No. PCT/US09/63983, mailed Feb. 25, 2010.
Search Report for European Patent Application No. 09150135.3, mailed Mar. 15, 2010.
Examination Report for New Zealand Patent Application No. NZ 589864, mailed Dec. 14, 2010.
Final Office Action for U.S. Appl. No. 11/679,331, mailed Feb. 15, 2011.
Search and Examination Report for British Patent Application No. 1104754.5, mailed May 18, 2011.
Office Action for Japanese Patent Application No. JP2009-502964, mailed May 23, 2011.
Search and Examination Report for British Patent Application No. 1108993.5, mailed Jun. 17, 2011.
Office Action for European Patent Application No. 09150135.3, mailed Jul. 11, 2011.
Office Action for Israel Patent Application No. 184552, mailed Jul. 28, 2011.
Office Action for U.S. Appl. No. 11/692,359, mailed Jul. 18, 2011.
Office Action for U.S. Appl. No. 12/119,016, mailed Nov. 3, 2011.
Office Action for U.S. Appl. No. 12/017,405, mailed Dec. 7, 2011.
Office Action for U.S. Appl. No. 12/615,636, mailed Jan. 25, 2012.
Examination Report for British Patent Application No. 1019599.8, mailed Feb. 7, 2012.
Office Action for Canadian Patent Application No. 2,644,547, mailed Feb. 14, 2014.
Non-Final Office Action for U.S. Appl. No. 13/924,037, mailed Feb. 13, 2014.

\* cited by examiner

DEVICES, SYSTEMS AND METHODS FOR MEDICAMENT DELIVERY

CROSS-REFERENCE TO RELATED APPLICATIONS

This application is a continuation of U.S. patent application Ser. No. 12/794,020, entitled "Devices, Systems and Methods for Medicament Delivery," filed Jun. 4, 2010, now U.S. Pat. No. 8,206,360 which is a continuation of U.S. patent application Ser. No. 11/621,236, now U.S. Pat. No. 7,731,686, entitled "Devices, Systems and Methods for Medicament Delivery," filed Jan. 9, 2007, which is a continuation-in-part of U.S. patent application Ser. No. 10/572,148, entitled "Devices, Systems and Methods for Medicament Delivery," filed Mar. 16, 2006, now U.S. Pat. No. 7,749,194, which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety. U.S. patent application Ser. No. 11/621,236 also claims priority to U.S. Provisional Application Ser. No. 60/787,046, entitled "Devices, Systems and Methods for Medicament Delivery," filed Mar. 29, 2006, which is incorporated herein by reference in its entirety.

BACKGROUND

The invention relates generally to a medical device, and more particularly to a medicament delivery device for delivering a medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

To actuate such a medicament delivery device, however, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. In certain instances, for example, users who have become confused in the operation of some known auto-injectors have inadvertently injected the medicament into their thumb by improperly positioning the auto-injector.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, and may therefore have no experience with the medicament delivery device. Similarly, because some known medicament delivery devices are configured to be used relatively infrequently in response to an allergic reaction or the like, even those users familiar with the device and/or who have been trained may not be well practiced at operating the device. Finally, such devices are often used during an emergency situation, during which even experienced and/or trained users may be subject to confusion, panic and/or the physiological effects of the condition requiring treatment.

Some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, inhalers or the like, can be compact, such printed instructions may be too small to read and comprehend during an emergency situation.

Some known medicament delivery devices include and electronic system to assist the user in setting the proper dosage and/or maintaining a compliance log. Such known medicament delivery devices and the accompanying electronic systems can be large and therefore not conveniently carried by the user. Moreover, such known medicament delivery devices and the accompanying electronic systems can be complicated and/or expensive to manufacture.

Thus, a need exists for a medicament delivery device and/or a medicament container that can be conveniently carried by a user, that provides instructions that can be easily understood by an untrained user in any type of situation, and that can be inexpensively manufactured.

SUMMARY

Medicament delivery devices are described herein. In one embodiment, an apparatus includes a label configured to be coupled to a medicament delivery device. The label includes a first surface and a second surface. The first surface is configured to be coupled to an outer surface of the medicament delivery device. The second surface includes a textual indicia. The label further includes an electronic circuit system configured to output an electronic signal.

DETAILED DESCRIPTION

Figure 1:
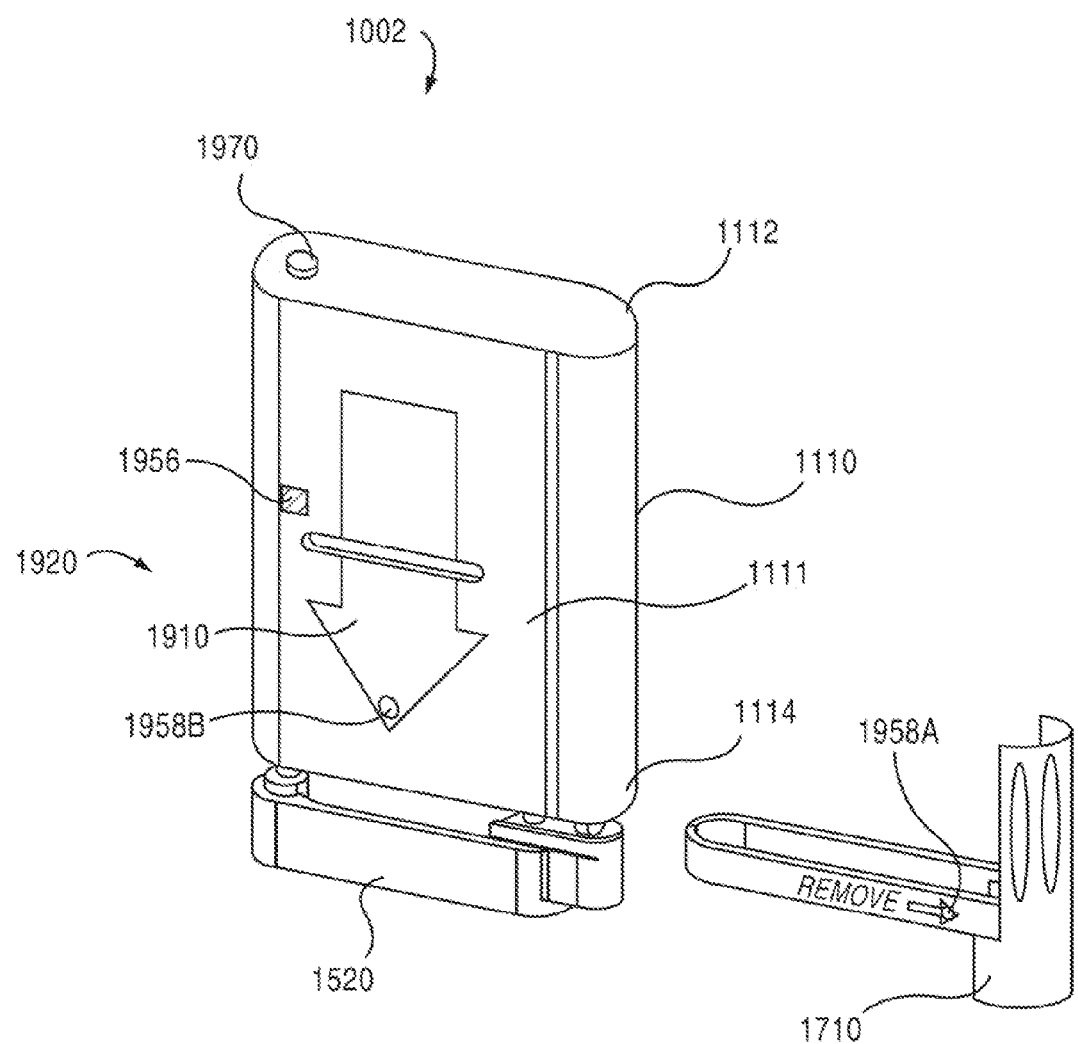
FIG. 1 is a perspective view of a medicament delivery device according to an embodiment of the invention.

In some embodiments, an apparatus includes a label configured to be coupled to a medicament delivery device. The label includes a first surface and a second surface. The first surface is configured to be coupled to an outer surface of the medicament delivery device. In some embodiments, for example, the first surface can include an adhesive. The second surface includes a textual indicia, such as, for example, a description of the medicament delivery device, a mark indicating the manufacturer or distributor of the medicament delivery device and/or an instruction associated with the use of the medicament delivery device. The label further includes an electronic circuit system configured to output an electronic signal. In some embodiments, the electronic signal can include an instruction associated with the use of the medicament delivery device.

In some embodiments, an apparatus includes a printed circuit board configured to be coupled to a medicament delivery device. The printed circuit board includes a substrate and an electrical conductor disposed on the substrate. The substrate includes an actuation portion configured to receive an actuator. The actuator is configured to deform the actuation portion of the substrate, thereby separating the electrical conductor.

In some embodiments, an apparatus includes a printed circuit board configured to be coupled to a medicament delivery device. The printed circuit board includes a substrate and an electrical conductor disposed on the substrate. The substrate includes an actuation portion configured to receive an actuator. The actuation portion of the substrate defines an opening adjacent the electrical conductor, the opening being configured to receive the actuator. The actuator is configured to move substantially parallel to a plane defined by a surface of the actuation portion of the substrate to produce a tear in the actuation portion of the substrate, thereby severing the electrical conductor. In some embodiments, the opening can be configured to propagate the tear in a predetermined direction.

In some embodiments, an apparatus includes a medicament delivery device configured to deliver a medicament into a body. The medicament delivery device, which can be, for example, a pen injector, an auto-injector, an inhaler or a transdermal delivery device, includes an electronic circuit system and a locking member. The electronic circuit system is configured to output an electronic signal associated with a use of the medicament delivery device. In some embodiments, the electronic signal can be, for example, associated with recorded speech. The locking member is configured to prevent the medicament from being delivered into the body. The locking member includes an actuator configured to actuate the electronic circuit system.

In some embodiments, an apparatus includes a medicament delivery device configured to deliver a medicament into a body. The medicament delivery device includes an electronic circuit system and a locking member. The electronic circuit system includes a switch and is configured to output a signal when the switch is moved from a first state to a second state. The locking member is configured to prevent the medicament from being delivered into the body when in a first position and to allow the medicament to be delivered into the body when in a second position. A portion of the locking member is configured to move the switch from the first state to the second state when the locking member is moved from the first position to the second position.

In some embodiments, an apparatus includes a housing configured to contain a medicament, a flexible printed circuit board, an energy storage member and a label. The flexible printed circuit board is disposed on an outer surface of the housing and includes a first electrical contact portion and a second electrical contact portion. The label is coupled to the flexible printed circuit board and the housing and is configured to maintain a first surface of the energy storage member in electrical communication with the first electrical contact portion and maintain a second surface of the energy storage member in electrical communication with the second electrical contact portion. The energy storage member, can be, for example, a battery.

In some embodiments, a method includes assembling a medicament delivery device, such as, for example, an auto-injector. An electronic circuit system is then placed against an outer surface of the medicament delivery device. A label is then coupled to the medicament delivery device such that the label is disposed about a portion of the electronic circuit system.

Figure 2:
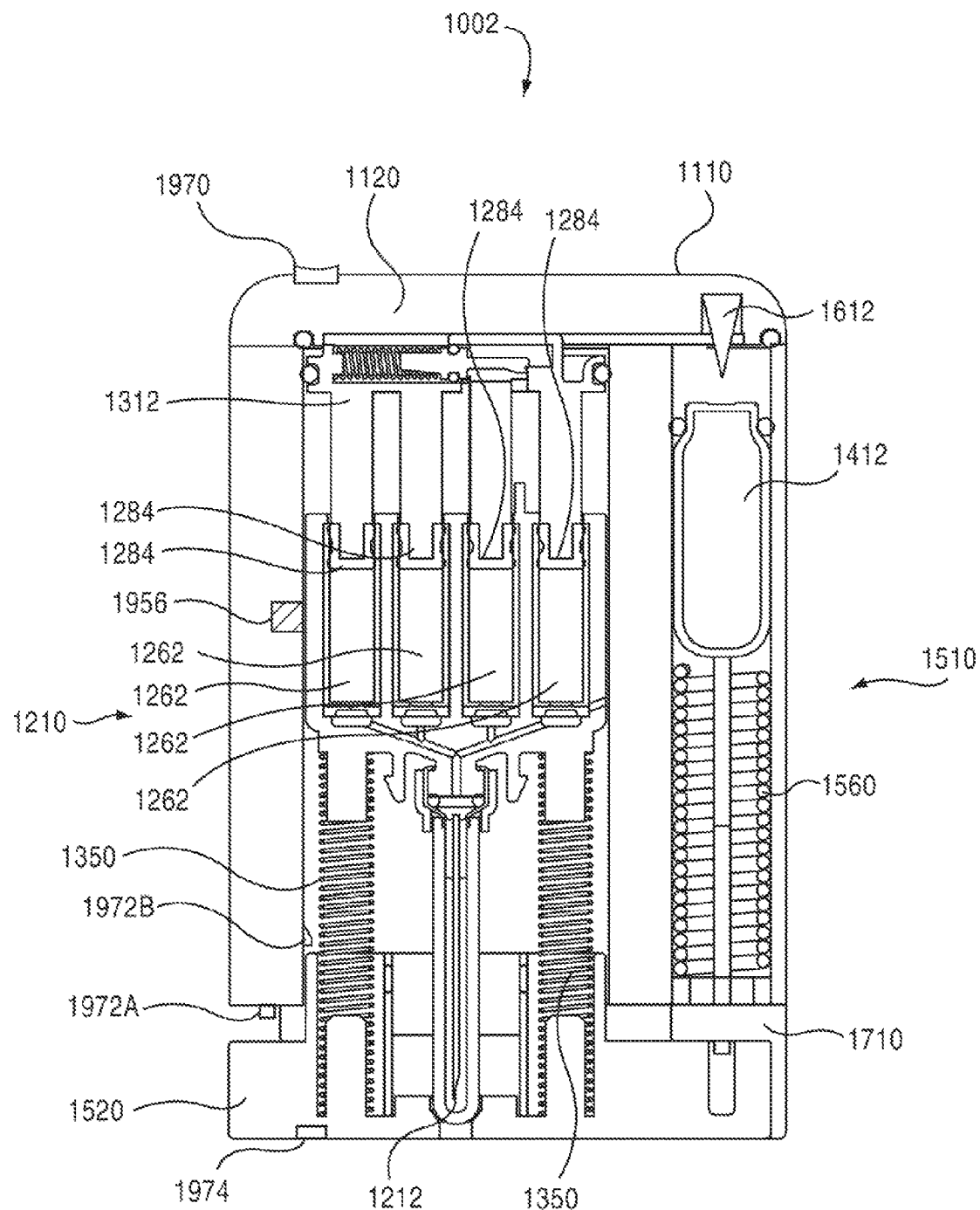
FIG. 2 is a front cross-sectional view of the medicament delivery device shown in FIG. 1.

FIGS. 1 and 2 are a perspective view and a partial cutaway front view, respectively, of an auto-injector 1002 according to an embodiment of the invention. The auto-injector 1002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, only an overview of the mechanical components and related operation of the auto-injector 1002 is included below.

The auto-injector 1002 includes a housing 1110 that defines a gas chamber 1120. The housing 1110 has a proximal end portion 1112 and a distal end portion 1114. A base 1520 is movably coupled to the distal end portion 1114 of the housing 1110. A safety lock 1710 is removably coupled to the base 1520. As discussed in more detail herein, when the safety lock 1710 is coupled to the base 1520, the auto-injector 1002 cannot be actuated. When the safety lock 1710 is removed from the base 1520, the base 1520 can be moved relative to the housing 1110, thereby actuating the auto-injector 1002. Accordingly, to inject a medicament into the body, the distal end portion 1114 of the housing 1110 is oriented towards the user such that the base 1520 is in contact with the portion of the body where the injection is to be made. The base 1520 is then moved towards the proximal end 1112 of the housing 1110 to actuate the auto-injector 1002.

The auto-injector 1002 includes a medicament injector 1210 and a system actuator 1510 disposed non-coaxially within the housing 1110. The medicament injector 1210 includes multiple medicament vials 1262, a plunger 1284 movably disposed within each medicament vial 1262, a movable member 1312 engaged with each plunger 1284 and a needle 1212. Retraction springs 1350 located within a portion of the base 1520 and the housing 1110 can push the needle 1212 back within the housing 1110 after injection. The system actuator 1510 includes a compressed spring 1560, a compressed gas cylinder 1412, and a puncturing mechanism 1612 to dispel the contents of the compressed gas cylinder 1412.

In use, when the auto-injector 1002 is actuated, the puncturing mechanism 1612 punctures the compressed gas cylinder 1412 allowing a pressurized gas to flow into the gas chamber 1120. In response to a force produced by the pressurized gas on the movable member 1312, the movable member 1312 moves distally within the housing 1110. As a result, the needle 1212 is extended through the housing 1110. The movement of the movable member 1312 also causes the plungers 1284 to move within the vials 1262, thereby expelling a medicament from the vials 1262.

The auto-injector 1002 includes an electronic circuit system 1920 to provide a predetermined sequence of electronic outputs during the use of the auto-injector 1002. The electronic circuit system 1920 is powered by a battery (not shown in FIGS. 1 and 2) and includes a processor (not shown in FIGS. 1 and 2), a start button 1970, two switches 1972A and 1972B, a proximity sensor 1974, two visual output devices 1958A and 1958B and an audio output device 1956. The components of the electronic circuit system 1920 are operatively coupled by any suitable mechanism, such as, for example, a printed circuit board (not shown in FIGS. 1 and 2) having conductive traces.

The start button 1970 is disposed on the proximal end of the housing 1110 and can be manually actuated by the user to begin the sequence of electronic outputs. The first switch 1972A is disposed on the distal portion 1114 of the housing 1110 adjacent the base 1520 and the locking member 1710. The locking member 1710 is configured to engage the first switch 1972A such that when the locking member 1710 is removed, as shown in FIG. 1, the first switch 1972A changes states. In this manner, removal of the locking member 1710 can trigger the processor to output a predetermined electronic output.

Similarly, the second switch 1972B is disposed on the housing 1110 adjacent the medicament injector 1210. The medicament injector 1210 is configured to engage the second switch 1972B such that when the medicament injector 1210 is moved distally within the housing 1110 the second switch 1972B changes states. In this manner, the processor can be prompted to output a predetermined electronic output based on the position of the medicament injector 1210.

The proximity sensor 1974 is disposed on the base 1520 and is configured to produce an output when the base 1520 engages the body. The proximity sensor can be, for example, a temperature sensor, an optical sensor or the like. In this manner, the processor can be prompted to output a predetermined electronic output when the base 1520 is positioned against the body.

The first visual output device 1958A is disposed on the locking member 1710. Similarly, the second visual output device 1958B is disposed on the outer surface 1111 of the housing 1110. The visual output devices 1958A and 1958B are in electronic communication with the processor and are configured to produce an output in response to an electronic signal output by the processor. The visual output devices 1958A and 1958B can be any suitable visual indicia, such as, light-emitting diodes (LEDs), liquid-crystal display (LCD) screens, optical polymers, fiber optic components or the like. In some embodiments, the visual output devices 1958A and 1958B can be coupled to the housing 1110 and/or the locking member 1710 by a label 1910.

The audio output device 1956 is disposed within the housing 1110 such that it can project sound outside of the housing 1110. The audio output device 1956 can be any suitable device for producing sound, such as a micro-speaker a piezoelectric transducer or the like. Such sound output can include, for example, an alarm, a series of beeps, recorded speech or the like. The audio output device 1956 is in electronic communication with the processor and is configured to produce an output in response to an electronic signal output by the processor.

In use, the user activates the electronic circuit system by pushing the start button 1970 to activate the processor, thereby causing the processor to output a predetermined sequence of electronic outputs. In some embodiments, the start button 1970 can activate the processor by providing an input to the processor. In other embodiments, the start button 1970 can activate the processor by placing the battery (not shown in FIGS. 1 and 2) in electronic communication with the processor.

In some embodiments, upon activation, the processor can output an electronic signal to the audio output device 1956 thereby producing a first electronic output instructing the user in how to use the auto-injector 1002. Such a message can state, for example, "please remove the safety tab." Additionally, the first visual output device 1958A can produce a flashing light to further indicate to the user where the locking member 1710 is located. The processor can be configured to repeat the first audible instruction if the locking member 1710 is not removed within a predetermined time period.

When the user removes the locking member 1710, the first switch 1972A changes states thereby triggering the processor to output an electronic output providing a second instruction to the user. The second instruction can be, for example, an audible speech output instructing the user to "please place the base of the device on the outer portion of your thigh." The first visual output device 1958A can produce a lighted output during this audible instruction, thereby visually indicating where the base 1520 is located and/or what portion of the base 1520 should be placed on the thigh.

When the user places the base 1520 against the body, the proximity sensor 1974 provides an input to the processor, thereby triggering the processor to output an electronic output providing a third instruction to the user. The third instruction can be, for example, an audible speech output instructing the user to "push down on the top of the device to activate the injector."

When the injection is completed, the medicament injector 1210 is configured to engage the second switch 1972B, thereby triggering the processor to output an electronic output providing a fourth instruction to the user. Such a post-use instruction can be, for example, an audible speech output instructing the user to seek further medical attention, providing instructions for the safe disposal of the auto-injector 1002 or the like.

Figure 3:
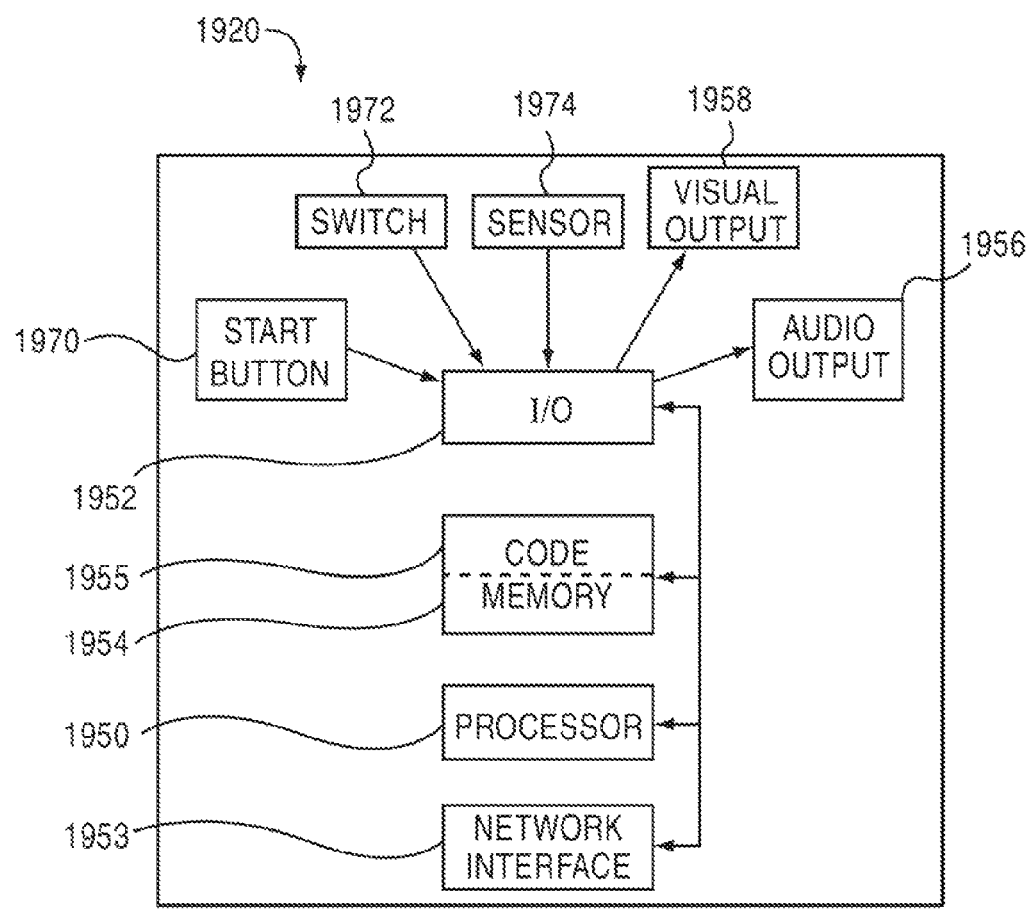
FIG. 3 is a schematic illustration of a portion of the medicament delivery device shown in FIG. 1.

FIG. 3 is a schematic illustration of the electronic circuit system 1920 of the auto-injector 1002. The electronic circuit system 1920 includes a processor 1950 operatively coupled to a memory device 1954. The memory device 1954 can be configured to store processor-readable code 1955 instructing the processor 1950 to perform the functions described above. In some embodiments, the processor-readable code 1955 can be modified and/or updated as circumstances dictate. The electronic circuit system 1920 includes an input/output device 1952 configured to receive electronic inputs from the switches 1972A and 1972B, the proximity sensor 1974 and/or the start button 1970. The input/output device 1952 is also configured to provide electronic signals to the various output devices, such as the visual output devices 1958A and 1958B and the audio output device 1956.

The electronic circuit system 1920 also includes a network interface 1953 configured to couple the electronic circuit system 1920 to a communications network. Such an arrangement can be used, for example, to download replacement processor-readable code 1955 from a central network (not shown) to the memory device 1954. The network interface 1953 can also be configured to transmit information from the electronic circuit system 1920 to a central network, the user's home computer, the user's cell phone or the like.

Figure 4:
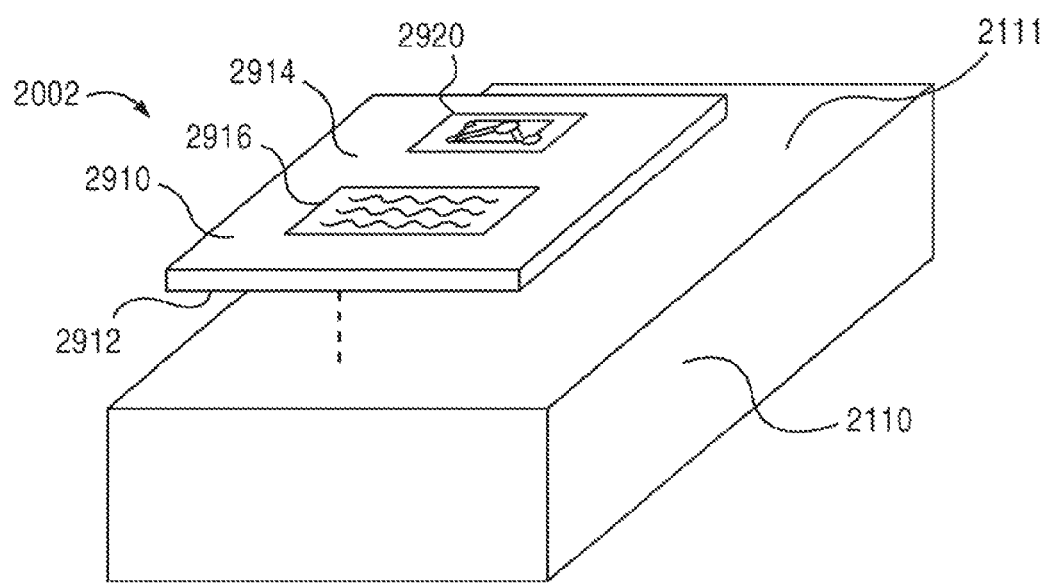
FIG. 4 is a schematic illustration of a medicament delivery device according to an embodiment of the invention.

FIG. 4 is a schematic illustration of a medical device 2002 according to an embodiment of the invention. The medical device 2002, which can be, for example, a medicament delivery device such as an auto-injector, a pen injector, an inhaler, a transdermal delivery system or the like, includes a housing 2110 and a label 2910. The label 2910 is coupled to an outer surface 2111 of the housing 2110. The label 2910 includes a first surface 2912, a second surface 2914 and an electronic circuit system 2920. The first surface 2912 is configured to engage the outer surface 2111 of the housing 2110 to couple the label 2910 to the housing 2110. In some embodiments, the first surface 2912 can include an adhesive to fixedly couple the label 2910 to the housing 2110. The second surface 2914 includes a textual indicia 2916. The textual indicia 2916 can include, for example, a description of the medicament delivery device, a source of the medicament delivery device and/or an instruction associated with the use of the medicament delivery device. Although the first surface 2912 is shown as being opposite the second surface 2914, in other embodiments, the first surface 2912 and the second surface 2914 can be adjacent each other and/or co-planar.

The electronic circuit system 2920 is configured to output an electronic signal. As discussed in more detail herein, the electronic circuit system 2920 can include many components, such as, for example, a processor, a switch, a visual output device and/or an audio output device. The electronic signal can be, for example, an electronic signal communicated to an output device, such as, for example, a visual output device, an audio output device, a haptic output device or the like. In some embodiments, the electronic signal can be associated with an aspect of the medical device 2002, such as an instruction associated with an initial use of the medical device 2002. For example, in some embodiments, the electronic circuit system 2920 can output a text message to a display screen (not shown) disposed on the medical device 2002 instructing the user in the use of the medical device 2002. In other embodiments, the electronic circuit system 2920 can produce an audio output, such as recorded speech, instructing the user in the use of the medical device 2002.

Although the electronic circuit system 2920 is shown as being disposed on the second surface 2914 of the label 2910, in other embodiments, the electronic circuit system can be disposed on the first surface 2912 of the label 2910. In yet other embodiments, the electronic circuit system 2920 can be disposed between the first surface 2912 and the second surface 2914 of the label 2910. In yet other embodiments, the label 2910 can include multiple discrete layers coupled together, within which portions of the electronic circuit system can be disposed.

Figure 5:
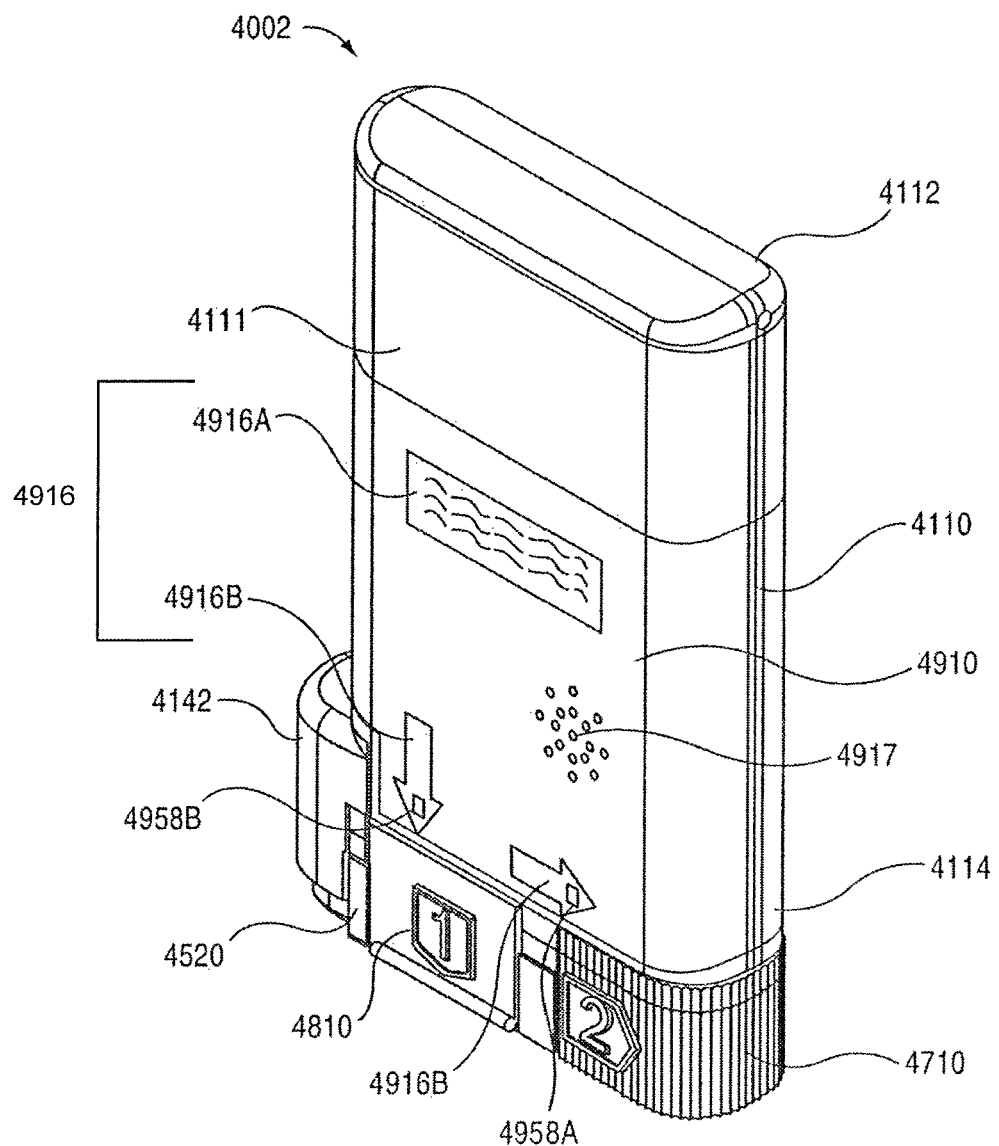
FIG. 5 is a perspective view of an auto-injector according to an embodiment of the invention.

FIG. 5 is a perspective view of an auto-injector 4002 according to an embodiment of the invention. The auto-injector 4002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, the mechanical components and operation of the auto-injector 4002 are not described in detail herein.

The auto-injector 4002 includes a housing 4110 having a proximal end portion 4112 and a distal end portion 4114. The distal end portion 4114 of the housing 4110 includes a protrusion 4142 to help a user grasp and retain the housing 4110 when using the auto-injector 4002. Said another way, the protrusion 4142 is configured to prevent the auto-injector 4002 from slipping from the user's grasp during use. A base 4520 is movably coupled to the distal end portion 4114 of the housing 4110. A needle guard assembly 4810 is removably coupled to the base 4520. Similarly, a safety lock 4710 is removably coupled to the base 4520. To inject a medicament into the body, the distal end portion 4114 of the housing is oriented towards the user such that the base 4520 is in contact with the portion of the body where the injection is to be made. The base 4520 is then moved towards the proximal end 4112 of the housing 4110 to actuate the auto-injector 4002.

Figure 26:
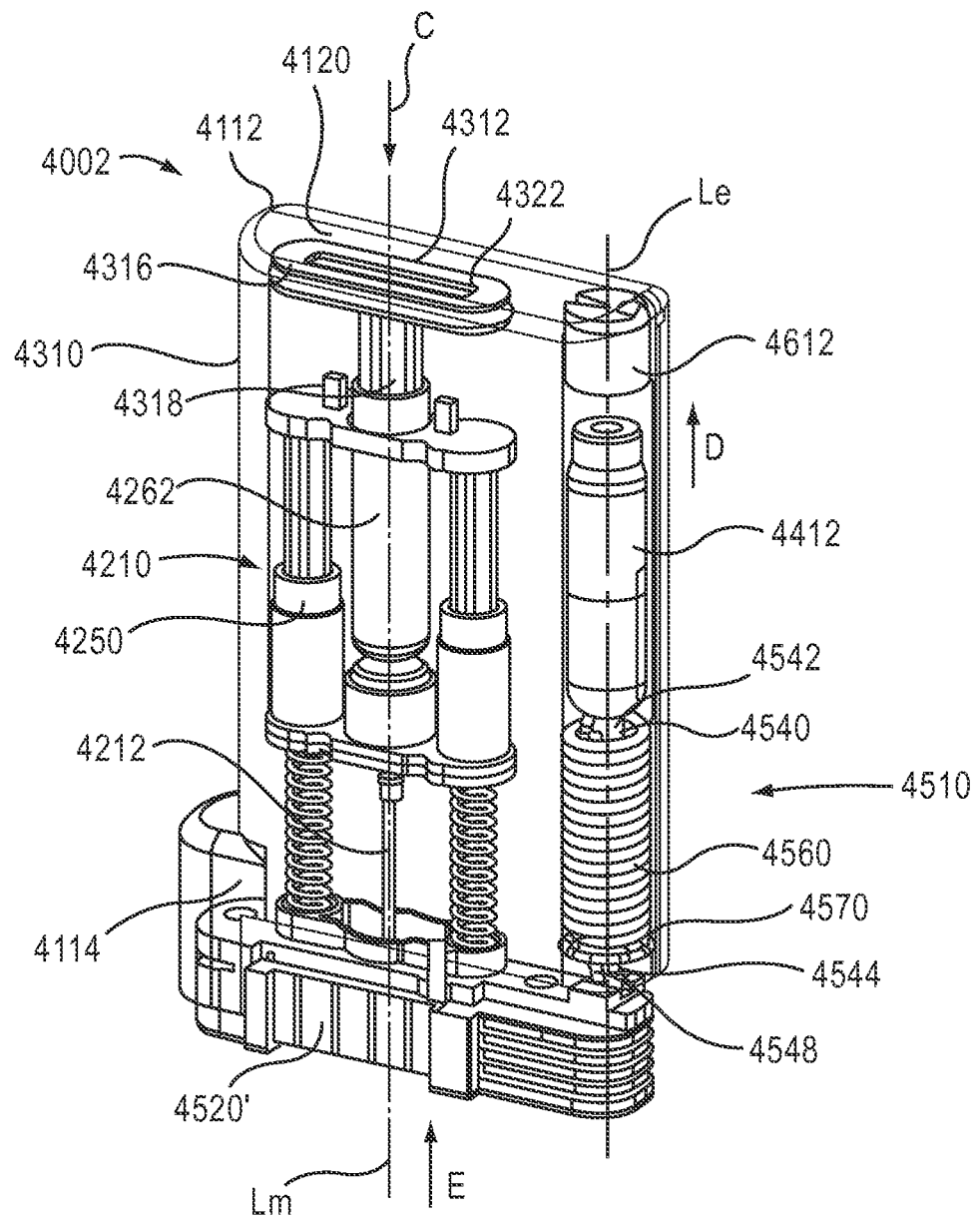
FIG. 26 is a perspective view of the auto-injector illustrated in FIG. 5 in a first configuration, with at least a portion of the auto-injector illustrated in phantom lines for ease of reference.
Figure 27:
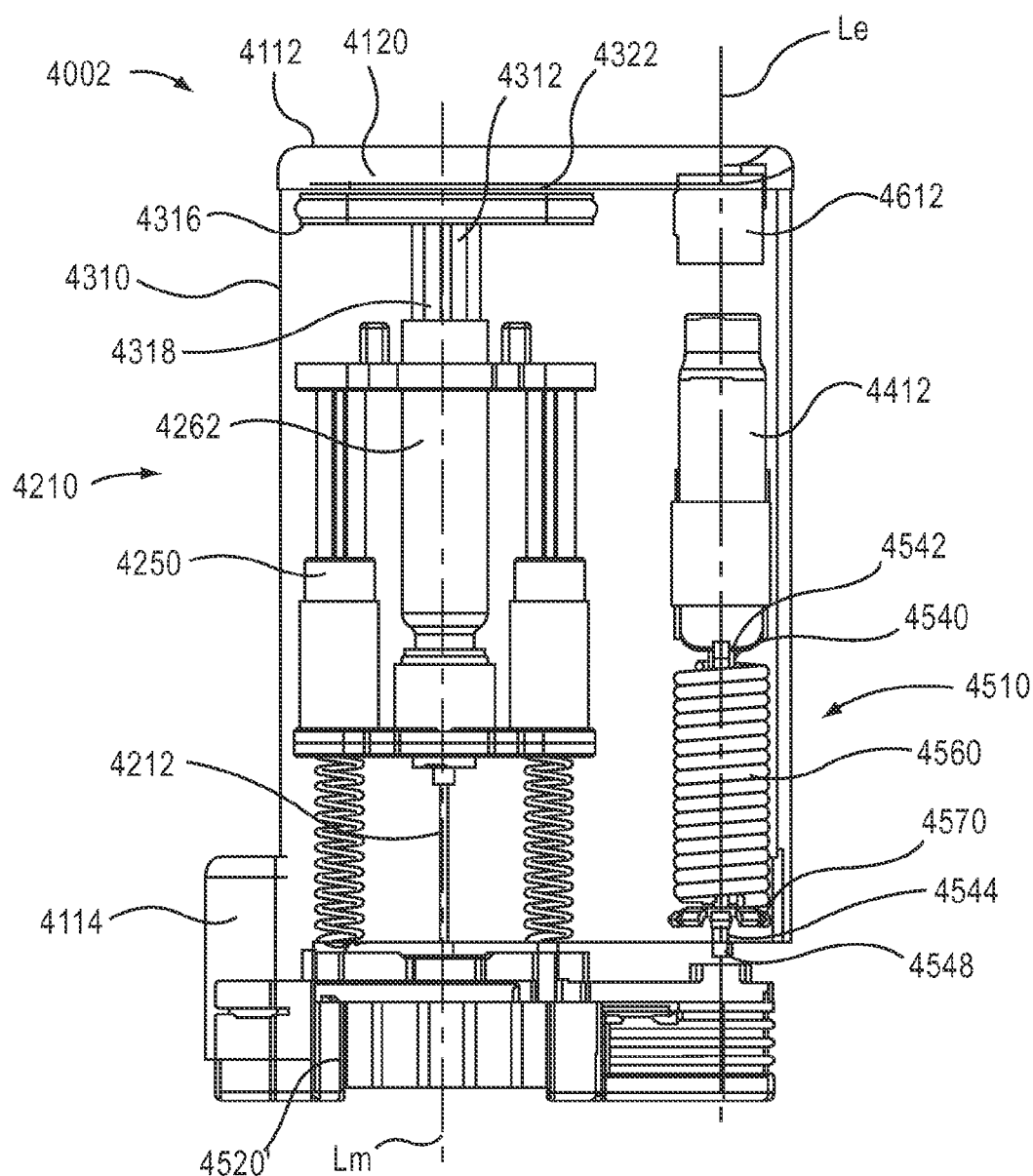
FIG. 27 is a front view of the auto-injector illustrated in FIGS. 5 and 26 in a first configuration.
Figure 28:
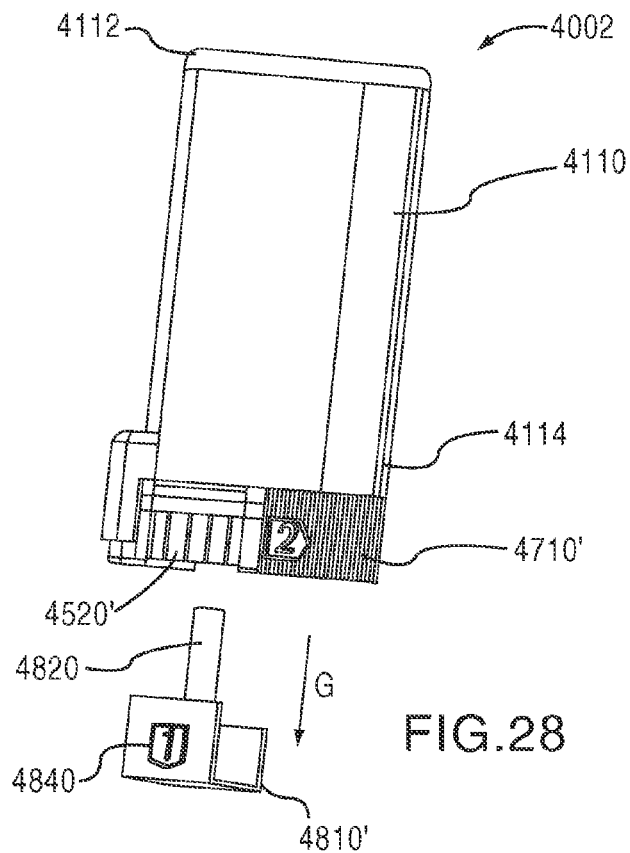
FIG. 28 is a perspective view of the auto-injector illustrated in FIG. 26 showing an assembly according to an embodiment of the invention being removed.
Figure 29:
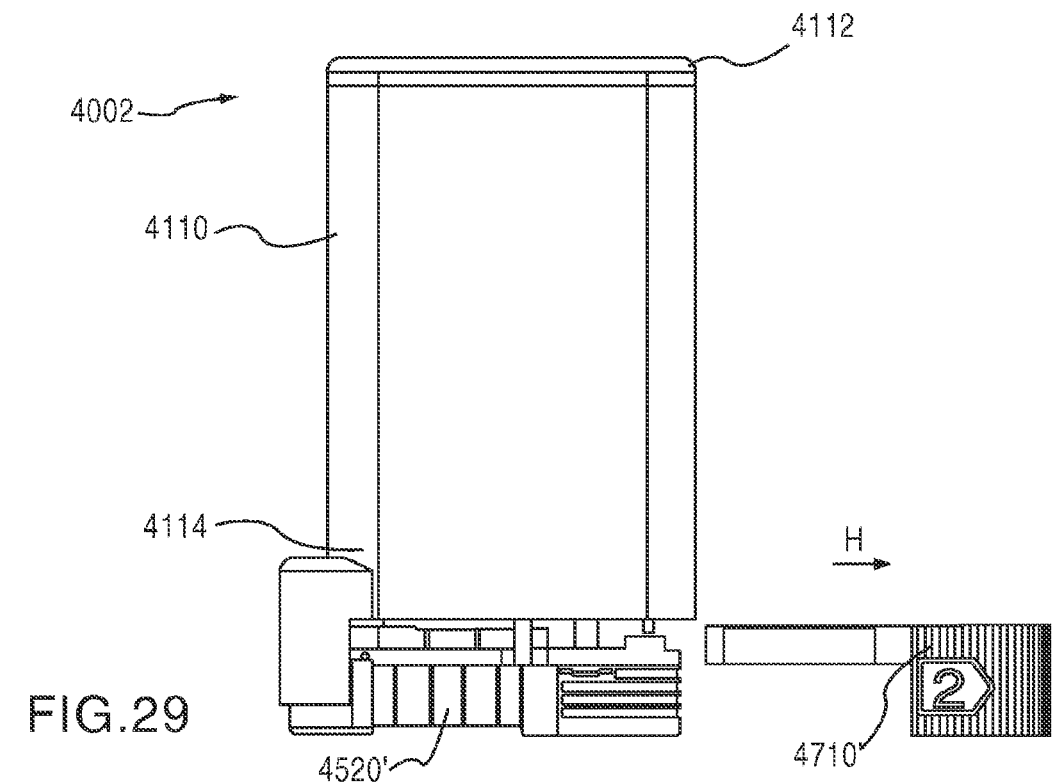
FIG. 29 is a front view of the auto-injector illustrated in FIG. 26 showing a member according to an embodiment of the invention being removed.

FIG. 26 is a perspective view of the auto-injector 4002 showing the housing 4110 in phantom lines so that the components contained within the housing 4110 can be more clearly seen. Similarly, FIG. 27 is a front view of the auto-injector 4002 showing the housing 4110 in phantom lines. For clarity, the auto-injector 4002 shown in FIGS. 26 and 27 show the auto-injector 4002 without the needle guard assembly 4810', the safety lock 4710' and the electronic circuit system 4920. Additionally, the auto-injector 4002 shown and described with reference to FIGS. 26-34 is presented to describe the mechanical components and operation of the device. Accordingly, the auto-injector 4002 shown and described with reference to FIGS. 26-34 includes a needle guard assembly 4810' that does not include a battery isolation tab 4860 (see e.g. FIG. 12), a safety lock 4710' that does not include an actuator 4732 (see e.g., FIG. 13), and a base 4520' that does not include an actuator 4538 (see e.g., FIG. 14).

The auto-injector 4002 includes a medicament injector 4210 and a movable member 4312 engaged with the medicament injector 4210, each of which are disposed within the housing 4110. The auto-injector 4002 also includes a system actuator 4510, a compressed gas container 4412 and a gas release mechanism 4612. The medicament injector 4210 includes a carrier 4250 that is movable within the housing 4110, a medicament container 4262 and a needle 4212. The medicament container 4262 is coupled to the carrier 4250. The needle 4212 is disposed within a needle hub portion of the carrier to allow the needle 4212 to be placed in fluid communication with the medicament container 4262 during an injection event.

The movable member 4312 includes a proximal end portion 4316 and a distal end portion 4318. The proximal end portion 4316 includes a surface 4322 that, together with the housing 4110, defines a gas chamber 4120. Said another way, the surface 4322 defines a portion of a boundary of the gas chamber 4120. The distal end portion 4318 is disposed within the medicament container 4262. In use, the movable member 4312 moves towards the distal end portion 4114 of the housing 4110, as indicated by arrow C in FIG. 26, in response to a force produced by a pressurized gas on the surface 4322 of the movable member 4312. As a result, the movable member 4312 and the medicament injector 4250 are moved towards the distal end portion 4114 of the housing 4110, thereby exposing the needle 4212 from the housing 4110. The movable member 4312 then continues to move within the medicament container 4262 to expel a medicament from the medicament container 4262 through the needle 4212.

The auto-injector 4002 is actuated by the system actuator 4510, which is configured to move the compressed gas container 4412 into contact with the gas release mechanism 4612. The gas release mechanism 4612 punctures a portion of the compressed gas container 4412 to release the pressurized gas contained therein into the gas chamber 4120 defined by the housing 4110. The system actuator 4510 includes a rod 4540, a spring 4560 and a spring retainer 4570. The rod 4540 has a proximal end portion 4542 and a distal end portion 4544. The proximal end portion 4542 of the rod 4540 is coupled to the compressed gas container 4412. The distal end portion 4544 of the rod 4540 is coupled to the spring retainer 4570 by two projections 4548, which can be moved inwardly towards each other to decouple the rod 4540 from the spring retainer 4570, as discussed below.

The spring 4560 is disposed about the rod 4540 in a compressed state such that the spring 4560 is retained by the proximal end portion 4542 of the rod 4540 and the spring retainer 4570. In this manner, the rod 4540 is spring-loaded such that when the distal end portion 4544 of the rod 4540 is decoupled from the spring retainer 4570, the force of the spring 4560 causes the rod 4540, and therefore the compressed gas container 4412, to move proximally as indicated by arrow D in FIG. 26 and into contact with the gas release mechanism 4612.

The base 4520' defines an opening 4522 configured to receive a portion of the projections 4548 when the base is moved towards the proximal end 4112 of the housing 4110, as indicated by arrow E in FIG. 26. When the projections 4548 are received within the opening 4522, they are moved together causing the distal end portion 4544 of the rod 4540 to be released from the spring retainer 4570.

As shown in FIGS. 26 and 27, the medicament injector 4210 defines a longitudinal axis Lm that is non-coaxial with the longitudinal axis Le defined by the compressed gas container 4412. Accordingly, the medicament injector 4210, the compressed gas container 4412 and the system actuator 4510 are arranged within the housing 4110 such that the housing has a substantially rectangular shape. Moreover, the non-coaxial relationship between the medicament injector 4210 and the compressed gas container 4412 allows the auto-injector 4002 to be actuated by manipulating the base 4520', which is located at the distal end portion 4114 of the housing 4110.

Prior to use, the auto-injector 4002 must first be enabled by first removing the needle guard 4810' and then removing the safety lock 4710'. As illustrated by arrow G in FIG. 28, the needle guard 4810' is removed by pulling it distally. As described in more detail below, removal of the needle guard 4810' also removes the isolation tab 4860 (see FIG. 12), thereby placing the batteries 4962 into electrical connection with the electronic circuit system 4910 (not shown in FIGS. 26-34, for purposes of clarity). Similarly, as illustrated by arrow H in FIG. 29, the safety lock 4710' is removed by pulling it substantially normal to the longitudinal axis Le of the compressed gas container 4412. Said another way, the safety lock 4710' is removed by moving it in a direction substantially normal to the direction that the needle guard 4810' is moved. As described below, removal of the safety lock 4710' also actuates the electronic circuit system 4920 (not shown in FIGS. 26-34, for purposes of clarity). The needle guard 4810' and the safety lock 4710' are cooperatively arranged to prevent the safety lock 4710' from being removed before the needle guard 4810' has been removed. Such an arrangement prevents the auto-injector 4002 from being actuated while the needle guard 4810' is in place.

Figure 30:
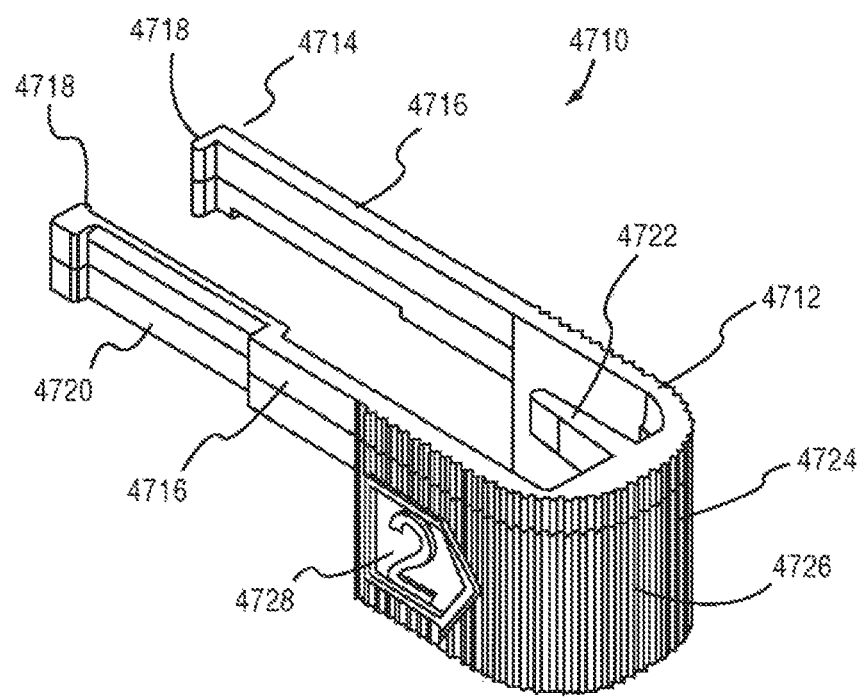
FIG. 30 is a perspective view of a member of the auto-injector illustrated in FIG. 29.
Figure 31:
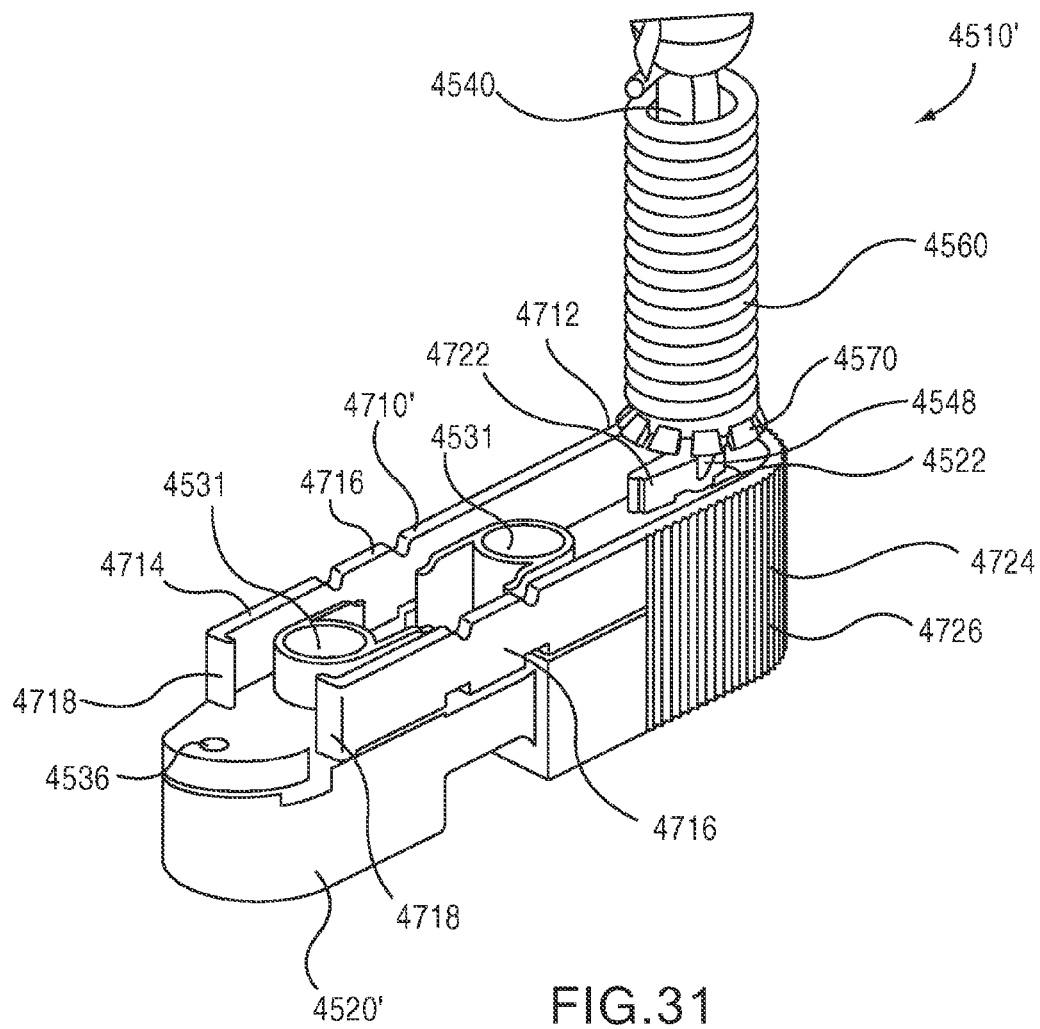
FIG. 31 is a perspective view of a portion of the auto-injector illustrated in FIG. 29.

As shown in FIG. 30, the safety lock 4710' is a U-shaped member having a first end 4712 and a second end 4714. The second end 4714 of the safety lock 4710' includes two extended portions 4716, each of which includes an inwardly facing protrusion 4718. When the safety lock 4710' is in its first (or locked) position, the extended portions 4716 extend around a portion of the base 4520' to space the base 4520' apart from the distal end portion 4114 of the housing 4110. As shown in FIG. 31, the protrusions 4718 are configured engage a portion of the base 4520' to removably couple the safety lock 4710' in its first position. Additionally, one of the extended portions 4716 defines a recess 4720 that receives the sheath retainer 4840 when the needle guard 4810' is in its first position.

The first end 4712 of the safety lock 4710' includes a locking protrusion 4722 that extends inwardly. As shown in FIG. 31, when the safety lock 4710' is in its first position, the locking protrusion 4722 extends between the projections 4548 of the rod 4540 and obstructs the opening 4522 of the base 4520'. In this manner, when the safety lock 4710' is in its first position, the base 4520' cannot be moved proximally to allow the projections 4548 to be received within the opening 4522. The arrangement of the locking protrusion 4722 also prevents the projections 4548 from being moved inwardly towards each other. Accordingly, when the safety lock 4710' is in its first position, the auto-injector 4002 cannot be actuated.

The outer surface 4724 of the first end 4712 of the safety lock 4710' includes a series of ridges 4726 to allow the user to more easily grip the safety lock 4710'. The outer surface 4724 of the first end 4712 of the safety lock 4710' also includes an indicia 4728 to instruct the user in operating the auto-injector 4002. As shown in FIG. 30, the indicia 4728 includes a numeral to indicate the order of operation and an arrow to indicate the direction in which the safety lock 4710' should be moved. In some embodiments, the indicia 4728 can include different colors, detailed instructions or any other suitable indicia to instruct the user. In other embodiments, the indicia 4728 can protrude from the safety lock 4710' to aid the user when grasping the safety lock 4710'.

Figure 32:
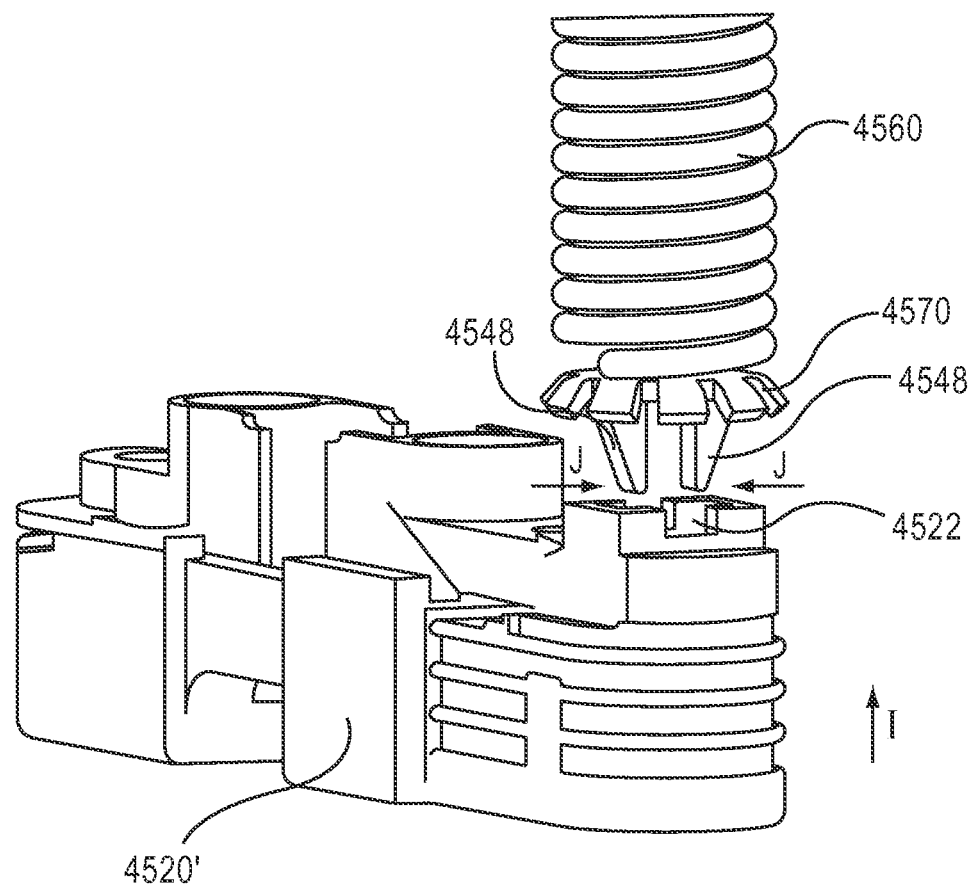
FIG. 32 is a perspective view of a portion of the auto-injector illustrated in FIG. 31.

After being enabled, the auto-injector 4002 can then be actuated by moving the base 4520' proximally towards the housing 4110; as indicated by arrow I in FIG. 32. Additionally, as described below, movement of the base 4520' actuates the electronic circuit system 4920 (not shown in FIGS. 26-34, for purposes of clarity).

Figure 33:
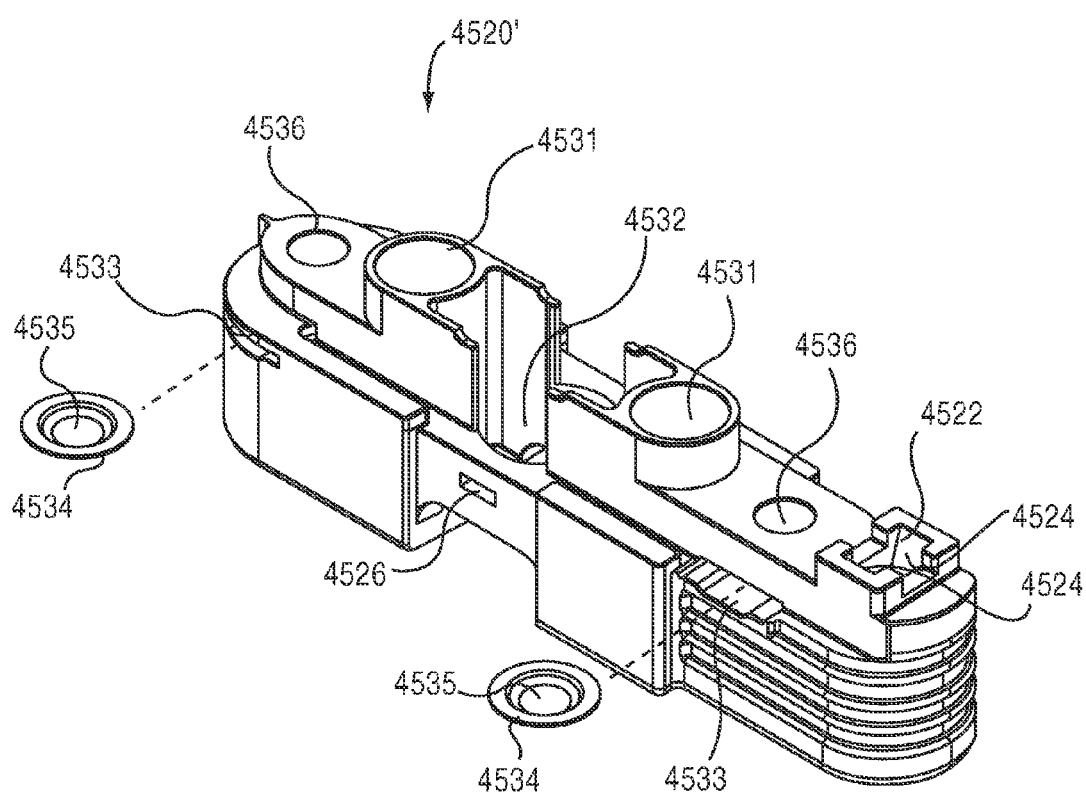
FIG. 33 is a partially exploded perspective view of a base of the auto-injector illustrated in FIG. 31.

As shown in FIG. 33, the base 4520' defines two openings 4536 that receive corresponding attachment protrusions 4150 disposed on the distal end portion 4114 of the housing 4110. In this manner, the movement and/or alignment of the base 4520' relative to the housing 4110 is guided by the attachment protrusions 4150 and the openings 4536. Each attachment protrusion 4150 is secured within its corresponding opening 4536 by a lock washer 4534. The lock washers 4534 each define an opening 4535 that receives a portion of the attachment protrusion 4150. The lock washers 4534 are disposed within slots 4533 defined by the base 4520' so that the openings 4535 are aligned with the attachment protrusions 4150. The openings 4535 are configured to allow the lock washers 4534 to move proximally relative to the attachment protrusions 4150, but to prevent movement of the lock washers 4534 distally relative to the attachment protrusions 4150. In this manner, when the attachment protrusions 4150 are disposed within the openings 4535 of the lock washers 4534, the base 4520' becomes fixedly coupled to the housing 4110. Moreover, after the base 4520' is moved proximally relative to the housing 4110, the lock washers 4534 prevent the base 4520' from returning to its initial position.

The base 4520' also defines a needle opening 4532, a recess 4526 and two retraction spring pockets 4531. The needle opening 4532 receives a portion of the needle guard 4810' when the needle guard is in its first position. Additionally, when the auto-injector 4002 is actuated, the needle 4212 extends through the needle opening 4532. The retraction spring pockets 4531 receive a portion of the retraction springs.

As shown in FIG. 33, the base 4520' includes two opposing tapered surfaces 4524 that define an opening 4522 configured to receive a corresponding tapered surface 4550 of the projections 4548 when the base 4520' is moved proximally towards the housing 4110. When the projections 4548 are received within the tapered opening 4522, they are moved together as indicated by arrows J in FIG. 32. The inward movement of the projections 4548 causes the rod 4540 to become disengaged from the spring retainer 4570, thereby allowing the rod 4540 to be moved proximally along its longitudinal axis as the spring 4560 expands.

Figure 34:
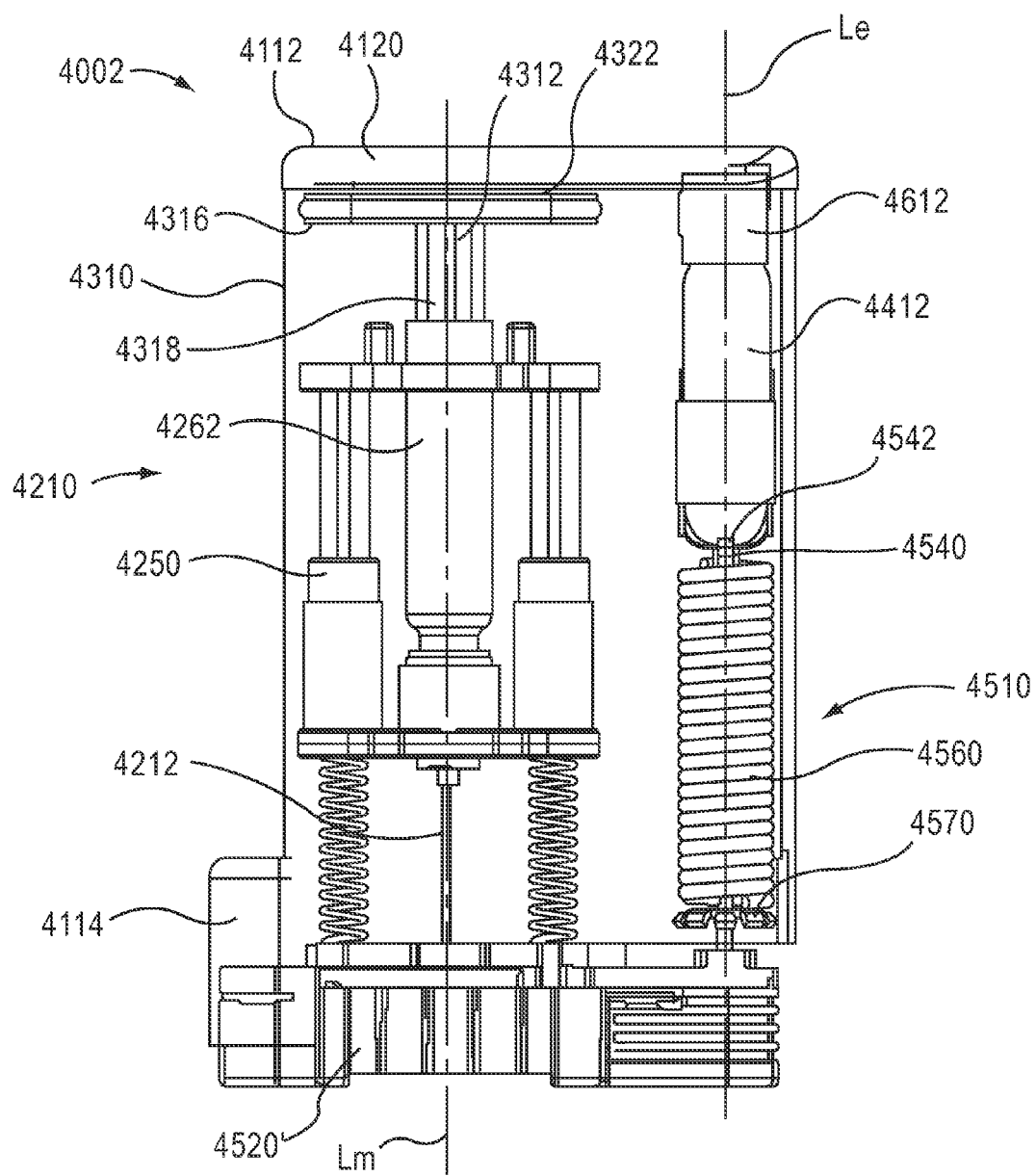
FIG. 34 is a front view of the auto-injector illustrated in FIG. 27 in a second configuration.

Because the rod 4540 is coupled to the compressed gas container 4412, when the rod 4540 is moved from its first (engaged) position to its second (actuated) position, the compressed gas container 4412 is moved proximally within the housing 4110 into engagement with the gas release mechanism 4612. FIG. 34 shows the auto-injector in a second configuration, in which the compressed gas container 4412 is engaged with the gas release mechanism 4612. When in the second configuration, the compressed gas contained within the compressed gas container 4412 is released to actuate the medicament injector 4210.

The pressurized gas produces a force that causes the movable member 4312 and the medicament injector 4210 to move distally within the housing 4110. The movement of the medicament injector 4210 causes the needle 4212 to extend from distal end portion 4114 of the housing 4110 and the base 4520. This operation can be referred to as the "needle insertion" operation. When the medicament injector 4210 has completed its movement (i.e., the needle insertion operation is complete), the movable member 4312 continues to move the medicament container 4262 distally within the carrier 4250. The continued movement of the medicament container 4262 places the needle 4212 in fluid communication with the medicament container 4262, thereby allowing the medicament to be injected. The force from the pressurized gas also causes the movable member 4312 to move within the medicament container 4262, thereby expelling the medicament through the needle 4212. This operation can be referred to as the "injection operation." Upon completion of the injection, the pressurized gas is released from the gas chamber 4120, thereby allowing the medicament injector 4210 and the movable member 4312 to be moved proximally within the housing. This operation can be referred to as the "retraction operation."

Figure 6:
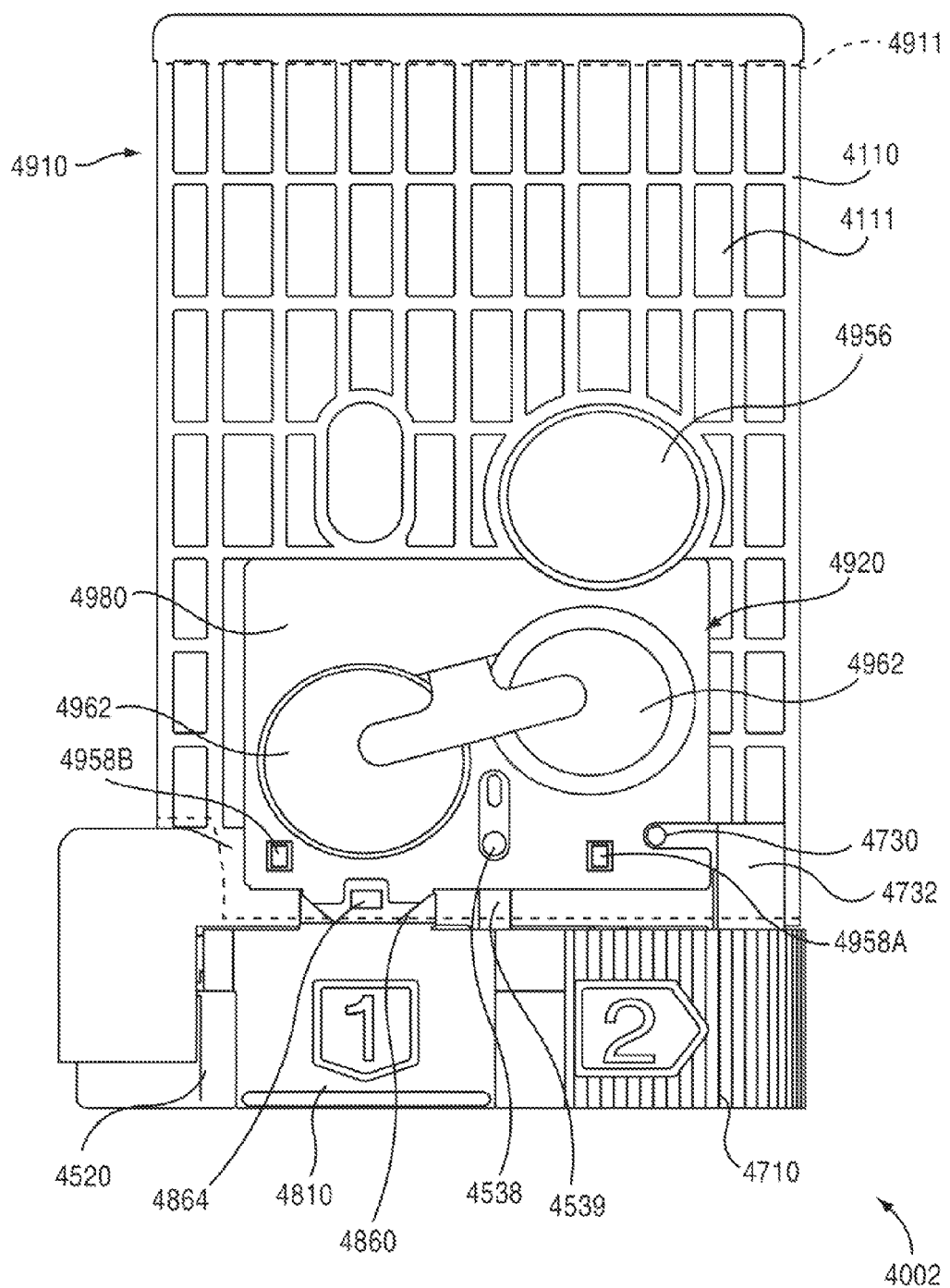
FIG. 6 is a front view of the auto-injector illustrated in FIG. 5, with a portion of the auto-injector illustrated in phantom lines for ease of reference.
Figure 7:
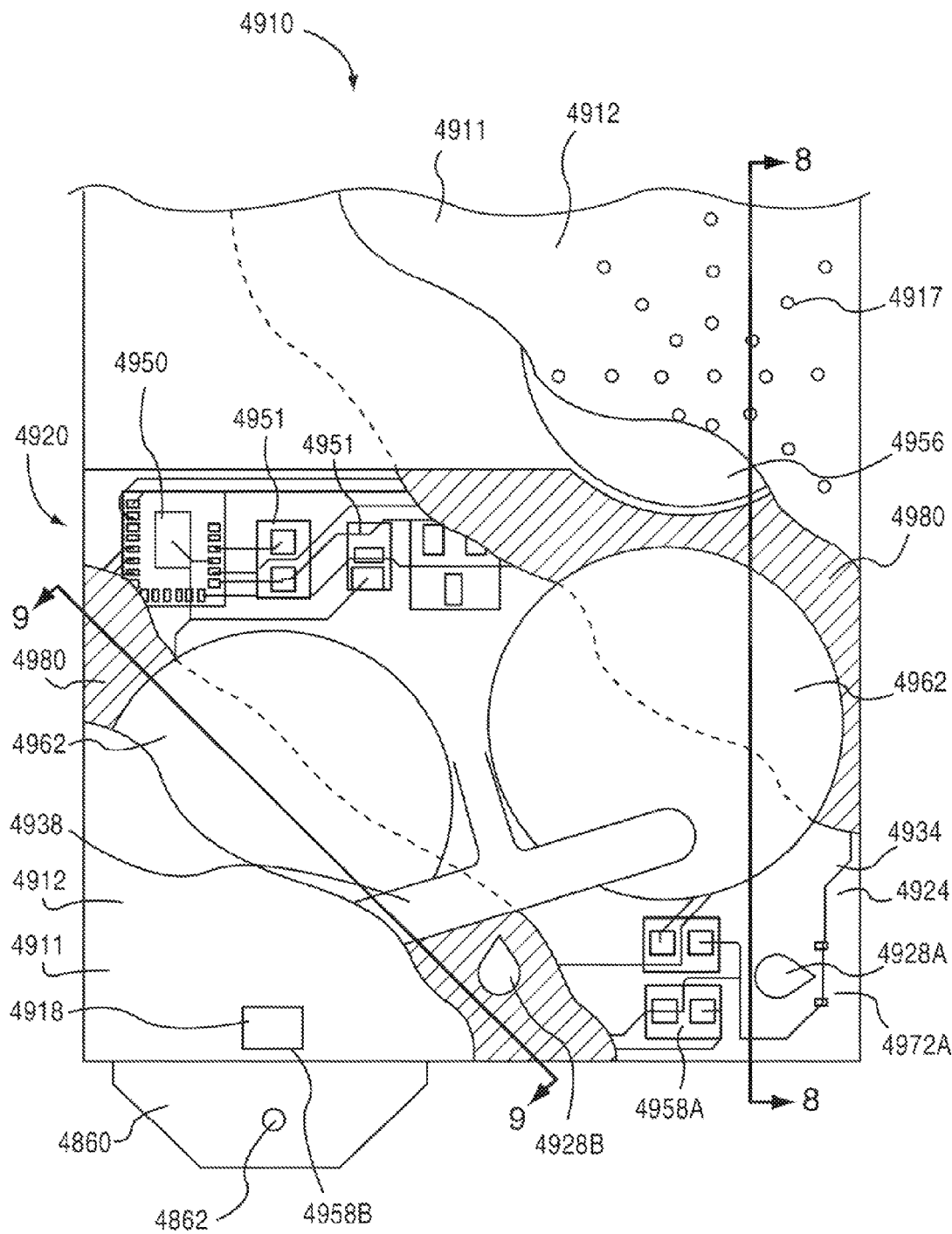
FIG. 7 is a partial cut-away front view of a portion of the auto-injector illustrated in FIG. 5.
Figure 8:
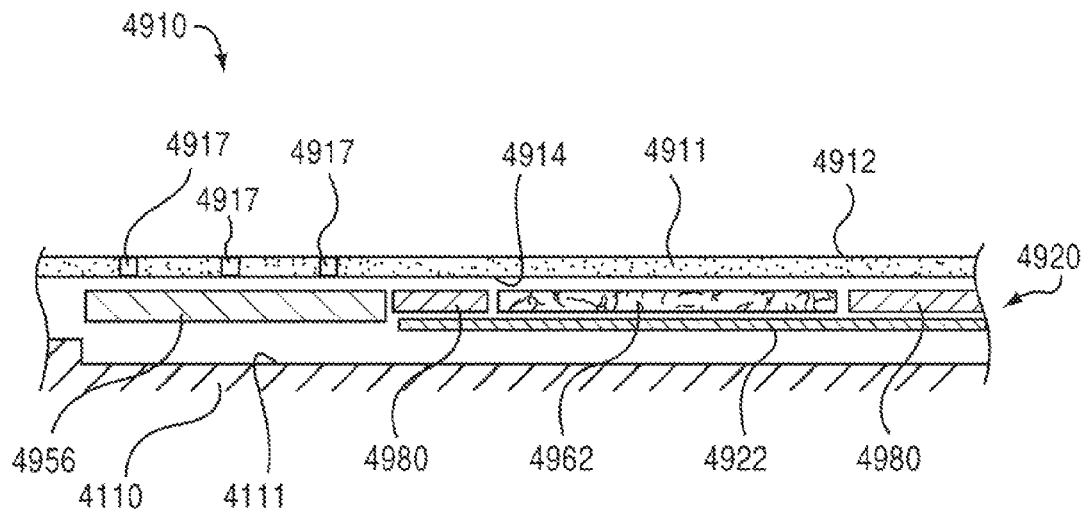
FIG. 8 is a cross-sectional view of a portion of the auto-injector illustrated in FIG. 5 taken along line 8-8 in FIG. 7.
Figure 9:
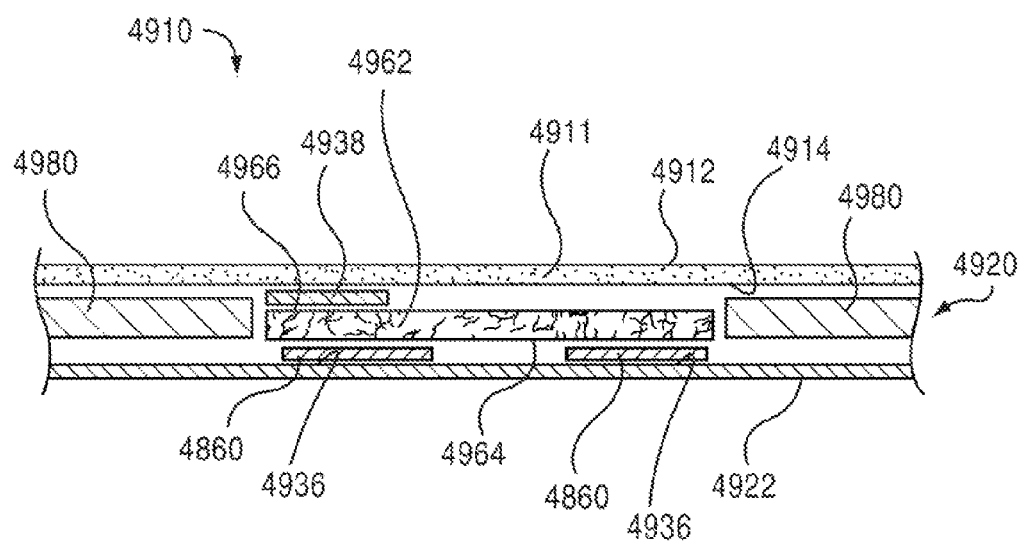
FIG. 9 is a cross-sectional view of a portion of the auto-injector illustrated in FIG. 5 taken along line 9-9 in FIG. 7.

The auto-injector 4002 includes a label 4910 coupled to an outer surface 4111 of the housing 4110. The label 4910 includes an outer layer 4911, an intermediate layer 4980 and an electronic circuit system 4920 (see FIGS. 7-9). FIG. 6 is a front view of the auto-injector 4002 showing the outer layer 4911 of the label 4910 in phantom lines so that the intermediate layer 4980 and an electronic circuit system 4920 can be more clearly seen. As shown in FIGS. 7-9, the outer layer 4911, which, in some embodiments, can be constructed from paper, has a first surface 4912 and a second surface 4914 opposite the first surface 4912. Multiple indicia 4916 are disposed on the first surface 4912. The indicia 4916 include a textual indicia 4916A and two symbolic indicia 4916B. The textual indicia 4916B can be written text describing the medicament delivery device, indicating a source of the medicament delivery device and/or instructing a user in the use of the medicament delivery device. The symbolic indicia 4916B can include, for example, arrows, pointers, trademarks, symbols describing the use of the medicament delivery device or the like. The label 4910 is coupled to the outer surface 4111 of the housing 4110 such that the portion of the first surface 4912 including the indicia 4916 is visible.

A portion of the second surface 4914 of the outer layer 4911 can be coupled to the outer surface 4111 of the housing 4110 by any suitable method. For example, in some embodiments, the second surface 4914 of the outer layer 4911 includes an adhesive configured to bond the outer layer 4911 to the outer surface 4111 of the housing 4110. Other portions of the second surface 4914 of the outer layer 4911 are adjacent the intermediate layer 4980 and portions of the electronic circuit system 4920. In this manner, the outer layer 4911 of the label 4910 retains the intermediate, or spacer, layer 4980 and the electronic circuit system 4920 in a predetermined position against the outer surface 4111 of the housing 4110.

The outer layer 4911 of the label 4910 includes multiple openings 4917 adjacent the audio output device 4956. In this manner, sound waves produced by the audio output device 4956 can be transmitted to an area outside of the housing 4110. Similarly, the outer layer 4911 of the label 4910 includes openings 4918 adjacent the light emitting diodes (LEDs) 4958A and 4958B to allow the user to see the visual output. In some embodiments, the outer layer 4911 of the label 4910 can include a transparent portion adjacent the LEDs 4958A and 4958B to allow the user to see the visual output.

The electronic circuit system 4920 includes a printed circuit board 4922 upon which a microprocessor 4950, two LEDs 4958A and 4958B, two switches 4972A and 4972B and various electronic components 4951, such as, for example, resistors, capacitors and diodes, are mounted. The electronic circuit system 4920 also includes an audio output device 4956, such as, for example, a micro-speaker, coupled to the outer surface 4111 of the housing 4110 adjacent the printed circuit board 4922. The printed circuit board 4922 includes a substrate 4924 upon which a series of electrical conductors 4934, such as for example, copper traces, are etched. The substrate 4924 can be constructed from any material having suitable electrical properties, mechanical properties and flexibility, such as, for example Mylar®, Kapton® or impregnated paper.

A mask layer (not shown) is disposed over the substrate 4924 to electrically isolate selected portions of the electrical conductors 4934 from adjacent components. The electrical conductors 4934 operatively couple the above-mentioned circuit components in a predetermined arrangement. In this manner, the electronic circuit system 4920 can be configured to output, via the LEDs 4958A and 4958B and/or the audio output device 4956, a predetermined sequence of electronic outputs during the use of the auto-injector 4002.

Power is supplied to the electronic circuit system 4920 by two batteries 4962 connected in series. The batteries can be, for example, three volt, "watch-style" lithium batteries. As shown in FIG. 9, each of the batteries 4962 has a first surface 4964 and a second surface 4966 opposite the first surface. The first surface 4964 can be, for example, an electrically negative terminal. Similarly, the second surface 4966 can be an electrically positive terminal. As discussed in more detail herein, the batteries 4962 are positioned such that a first electrical contact portion 4936 of the printed circuit board 4922 can be placed in contact with the first surface 4964 of the battery 4962 and a second electrical contact portion 4938 of the printed circuit board 4922 can be placed in contact with the second surface 4966 of the battery 4962. In this manner, the batteries 4962 can be operatively coupled to the electronic circuit system 4920.

As shown in FIGS. 7 and 9, a battery isolation tab 4860 is movably disposed between the first electrical contact portion 4936 of the printed circuit board 4922 and the first surface 4964 of one of the batteries 4962. The battery isolation tab 4860 can be constructed from any electrically isolative material, such as, for example, Mylar®. As discussed in more detail herein, in this manner, the batteries 4962 can be selectively placed in electronic communication with the electronic circuit system 4920.

The intermediate, or spacer, layer 4980 is disposed between the outer layer 4911 and the electronic circuit system 4920. The intermediate layer 4980 includes openings (not shown) within which various components of the electronic circuit system, such as, for example, the batteries 4962 are disposed. The intermediate layer 4980 is sized to maintain a predetermined spacing between the various components included in the label 4910. The intermediate layer can be constructed from any suitable material, such as, for example, flexible foam having an adhesive surface, polycarbonate or the like.

Figure 10:
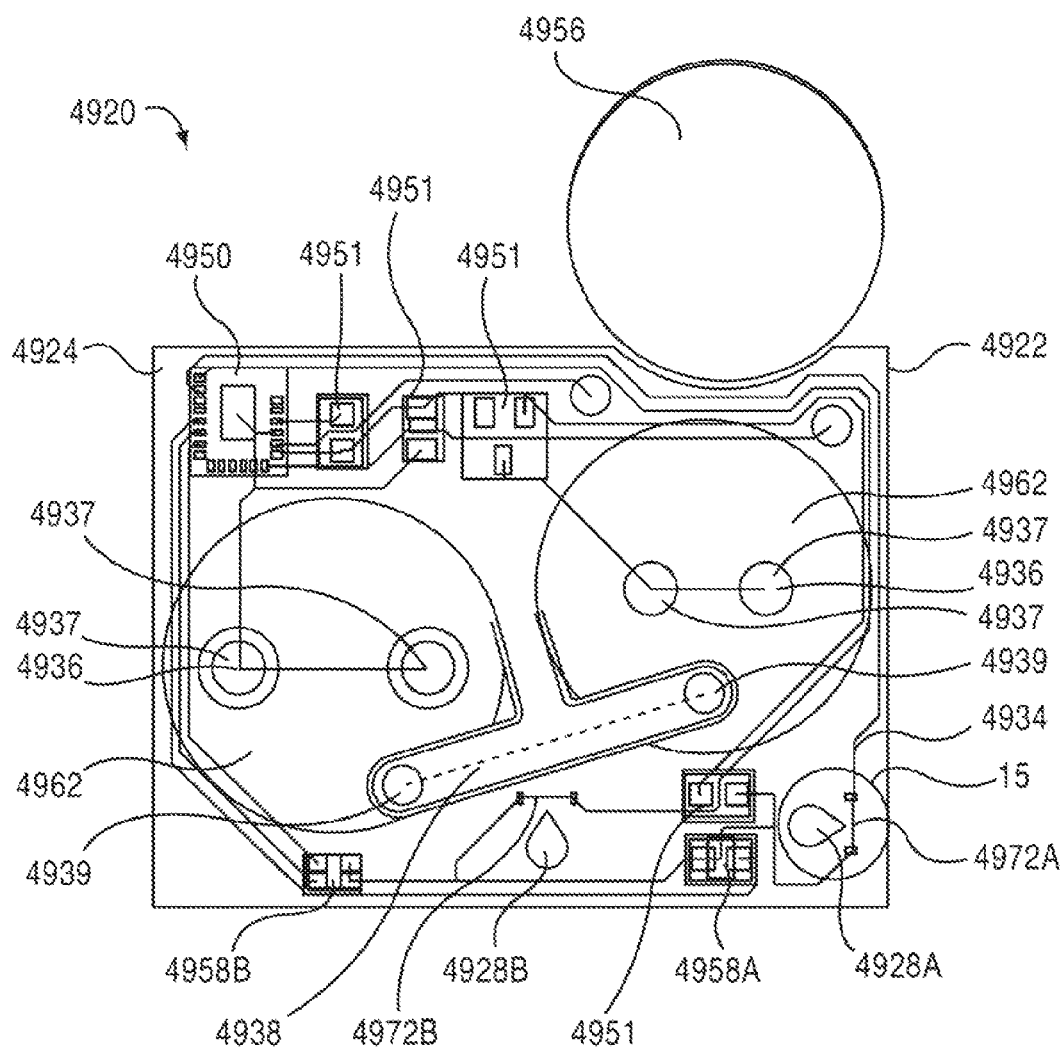
FIG. 10 is a front view of a portion of the auto-injector illustrated in FIG. 5.
Figure 11:
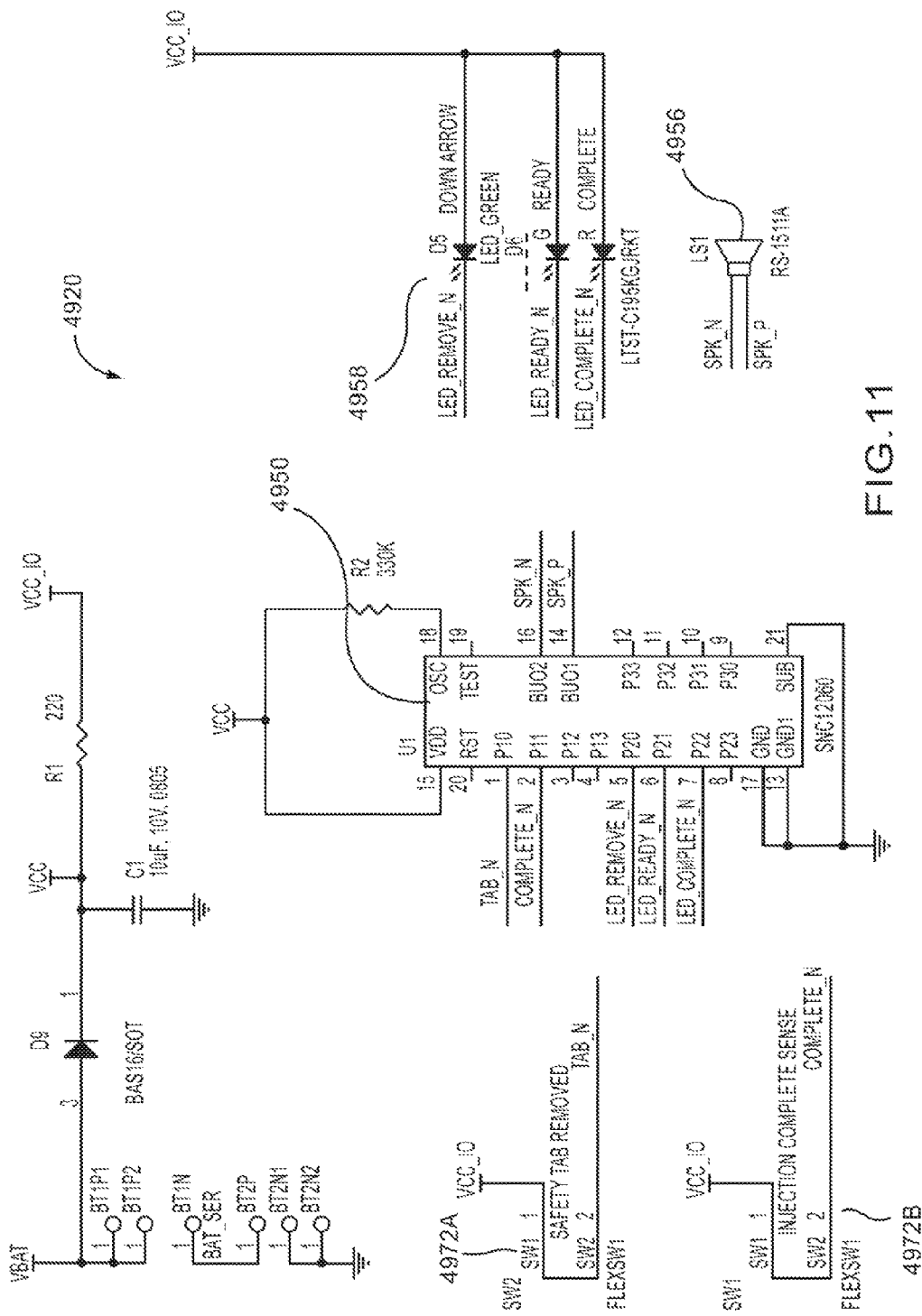
FIG. 11 is a schematic illustration of a portion of the auto-injector illustrated in FIG. 5.

FIG. 10 is a front view of the electronic circuit system 4920 showing the arrangement of the various components (i.e., the microprocessor 4950, LEDs 4958A and 4958B, switches 4972A and 4972B, audio output device 4956 or the like). FIG. 11 is a schematic illustration of the electronic circuit system 4920.

The operation of the auto-injector 4002 and the electronic circuit system 4920 is now discussed with reference to FIGS. 12-14. The actuation of the electronic circuit system 4920 includes several operations that are incorporated into the standard procedures for using the auto-injector 4002. In this manner, the user can actuate the electronic circuit system 4920 without completing any additional operations.

Figure 12:
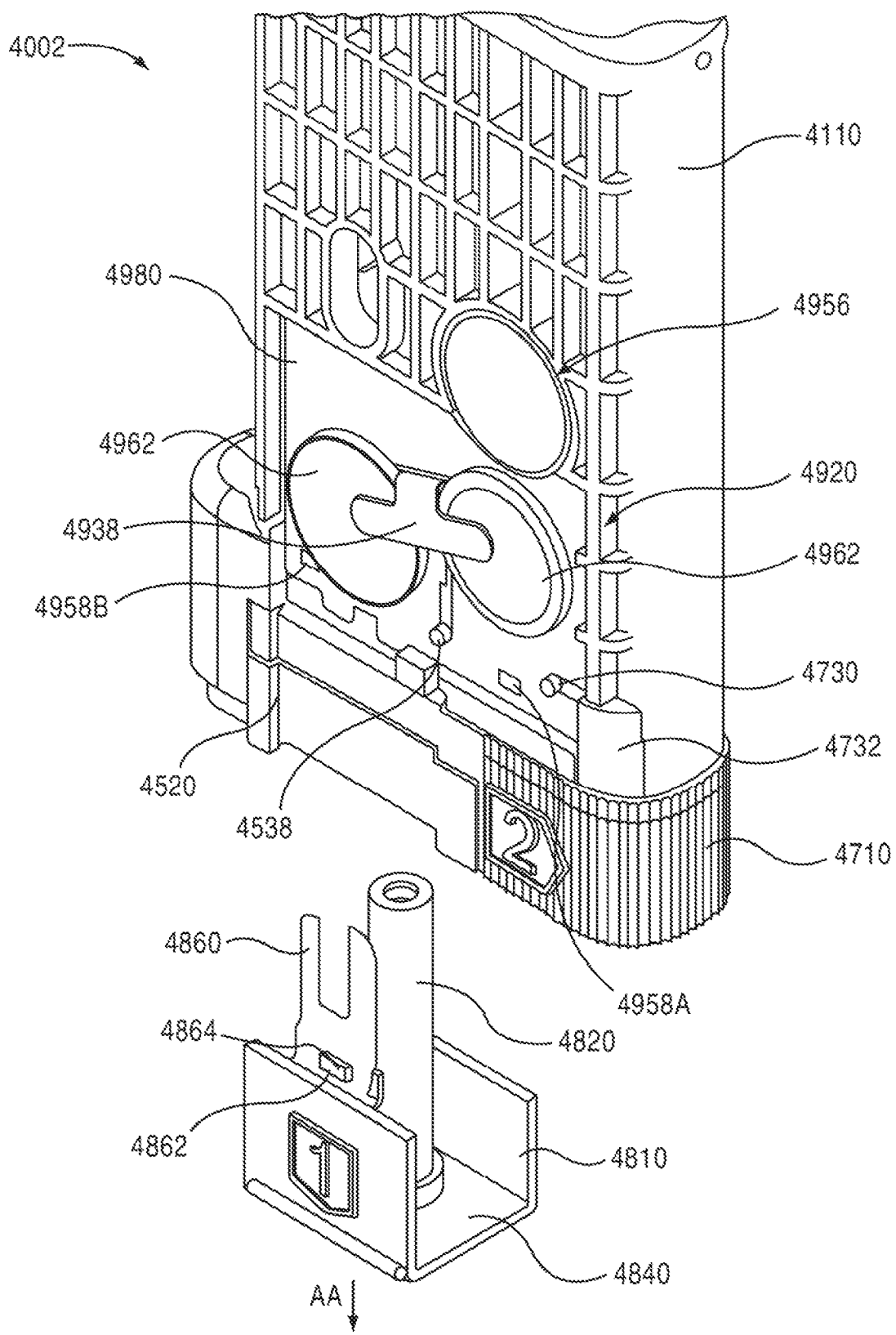
FIG. 12 is a perspective view of a portion of the auto-injector illustrated in FIG. 5 in a second configuration.
Figure 13:
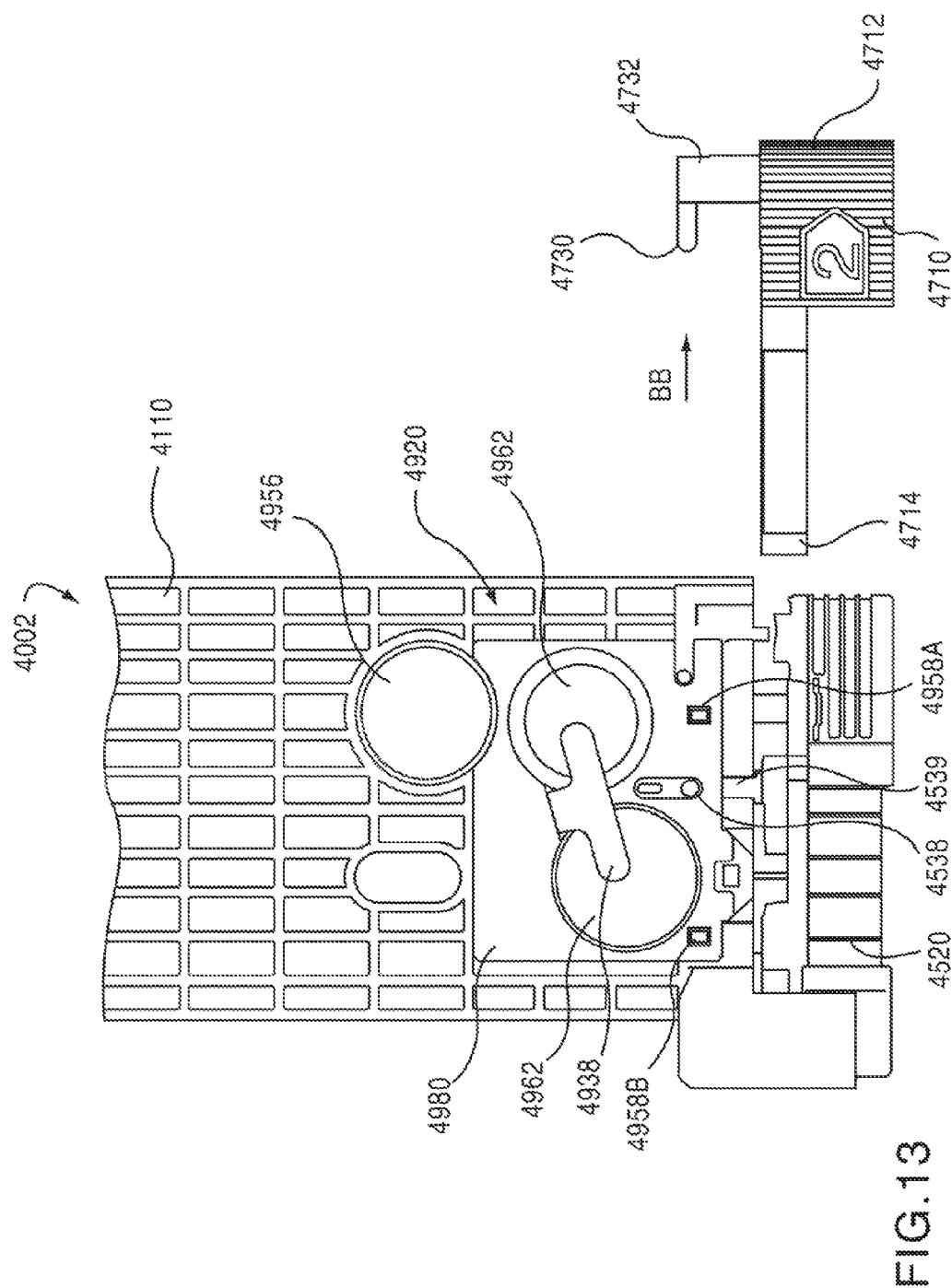
FIG. 13 is a perspective view of a portion of the auto-injector illustrated in FIG. 5 in a third configuration.

Prior to use, the auto-injector 4002 is first enabled by removing the needle guard 4810 and the safety lock 4710 (see FIGS. 12 and 13). As illustrated by arrow AA in FIG. 12, the needle guard 4810 is removed by moving it distally. The needle guard 4810 includes a sheath retainer 4840 and a sheath 4820. The sheath 4820 is configured to receive a portion of the needle (not shown) when the needle guard 4810 is in a first (or installed) position. The sheath retainer 4840 is coupled to the sheath 4820 such that when the sheath retainer 4840 is moved distally away from the base 4520 into a second (or removed) position, the sheath 4820 is removed from the needle.

The sheath retainer 4840 includes an actuator 4864 that is received by an opening 4862 in the isolation tab 4860. Accordingly, when the sheath retainer 4840 is moved distally away from the base 4520, the isolation tab 4860 is removed from the area between the first electrical contact portion 4936 of the printed circuit board 4922 and the first surface 4964 of one of the batteries 4962. In this manner, the batteries 4962 can be operatively coupled to the electronic circuit system 4920 when the needle guard 4810 is removed, thereby actuating the electronic circuit system 4920.

When actuated, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a .WAV file that contains a recorded instruction instructing the user in the operation of the auto-injector 4002. Such an instruction can state, for example, "remove the blue safety tab near the base of the auto-injector." The processor can simultaneously output an electronic signal to the first LED 4958A, thereby causing the first LED 4958A, which is located near the safety lock 4710, to flash a particular color. In this manner, the electronic circuit system 4920 can provide both audible and visual instructions to assist the user in the initial operation of the auto-injector 4002.

In other embodiments, the electronic circuit system 4920 can output an electronic output associated with a description and/or status of the auto-injector 4002 and/or the medicament contained therein. For example, in some embodiments, electronic circuit system 4920 can output an audible message indicating the type of medicament contained in the auto-injector, the expiration date of the medicament, the dosage of the medicament or the like.

As illustrated by arrow BB in FIG. 13, the safety lock 4710 is removed by moving it substantially normal to the longitudinal axis of the housing 4110. The safety lock 4710 has a first end 4712 and a second end 4714. When the safety lock 4710 is in its first (or locked) position, the second end 4714 extends around a portion of the base 4520 to space the base 4520 apart from the distal end portion 4114 of the housing 4110. Additionally, the first end 4712 includes a locking protrusion (not shown) that obstructs portions of the system actuator (not shown) further preventing the base 4520 from being moved proximally towards the housing 4110. Accordingly, when the safety lock 4710 is in its first position, the auto-injector 4002 cannot be actuated.

Figure 15:
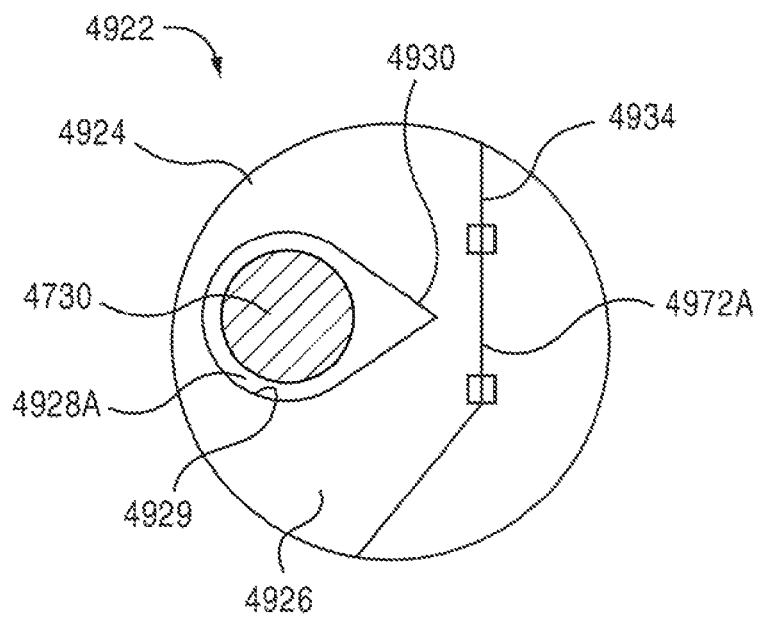
FIGS. 15 and 16 are front views of a portion of the auto-injector labeled as region 15 in FIG. 10, in a first configuration and a second configuration, respectively.
Figure 16:
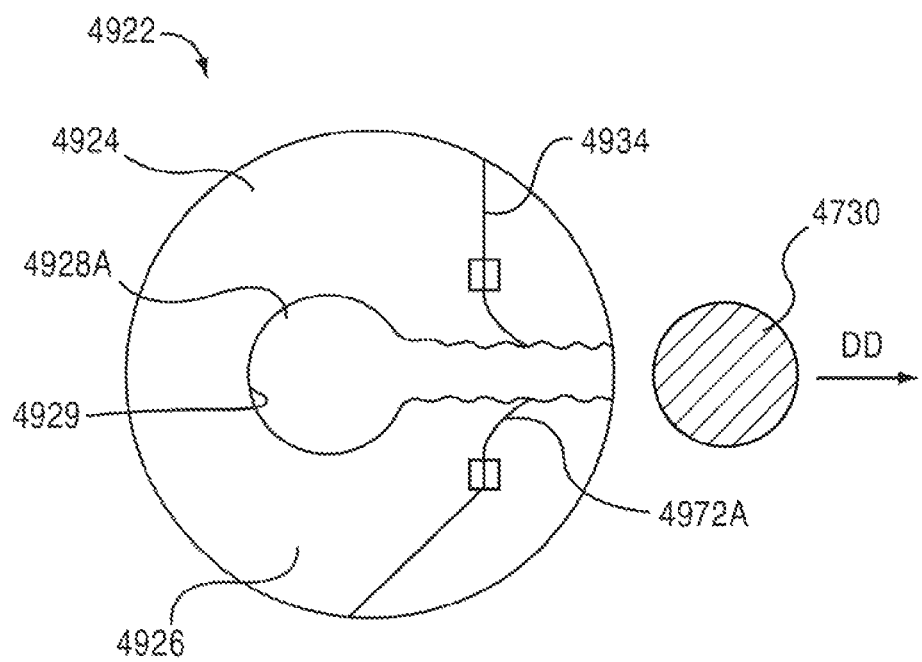

In some embodiments, the safety lock 4710 includes an actuator 4732 that actuates the electronic circuit 4920 to trigger a predetermined output or sequence of outputs when the safety lock 4710 is moved from the first position to a second (or unlocked) position, as shown in FIG. 13. More particularly, as shown in FIGS. 10, 15 and 16, the actuator 4732 includes a protrusion 4730 that is received within a first opening 4928A defined by an actuation portion 4926 of the substrate 4924 when the safety lock 4710 is in the first position. The boundary 4929 of the first opening 4928A has a discontinuous shape, such as, for example, a teardrop shape, that includes a stress concentration riser 4930. The discontinuity and/or the stress concentration riser 4930 of the boundary 4929 can be of any suitable shape to cause the substrate 4924 to deform in a predetermined direction when the protrusion 4730 is moved relative to the first opening 4928A.

As shown in FIGS. 15 and 16, the first opening 4928A is defined adjacent an electrical conductor 4934 that, as discussed above, electronically couples the components included in the electronic circuit system 4920. The electrical conductor 4934 includes a first switch 4972A, which can be, for example a frangible portion of the electrical conductor 4934. In use, when the safety lock 4710 is moved from the first position to the second position, the actuator 4732 moves in a direction substantially parallel to a plane defined by a surface of the actuation portion 4926 of the substrate 4924. The movement of the actuator 4732 causes the protrusion 4730 to move within the first opening 4928A, as indicated by the arrow DD in FIG. 16. The movement of the protrusion 4730 tears the actuation portion 4926 of the substrate 4924, thereby separating the portion of the electrical conductor 4934 including the first switch 4972A. Said another way, when the safety lock 4710 is moved to the second position, the actuator 4732 moves irreversibly the first switch 4972A from a first state (e.g., a state of electrical continuity) to a second state (e.g., a state of electrical discontinuity).

When the actuator 4732 actuates the electronic circuit system 4920 as described above, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user of the status of the auto-injector 4002. Such a status message can state, for example, "The auto-injector is now enabled." The processor can also simultaneously output an electronic signal to the first LED 4958A, thereby causing the first LED 4958A to stop flashing, change color or the like.

In some embodiments, the electronic circuit system 4920 can be configured to output the status message for a predetermined time period, such as, for example, five seconds. After the predetermined time period has elapsed, the electronic circuit system 4920 can output an audible message further instructing the user in the operation of the auto-injector 4002. Such an instruction can state, for example, "Place the base of the auto-injector against the patient's thigh. To complete the injection, press the base firmly against the patient's thigh." In some embodiments, the processor can simultaneously output an electronic signal to the second LED 4958B, thereby causing the second LED 4958B, which is located near the base 4520, to flash a particular color. In this manner, the electronic circuit system 4920 can provide both audible and visual instructions to assist the user in the placement and actuation of the auto-injector 4002. In some embodiments, the electronic circuit system 4920 can be configured to repeat the instructions after a predetermined time period has elapsed.

Figure 14:
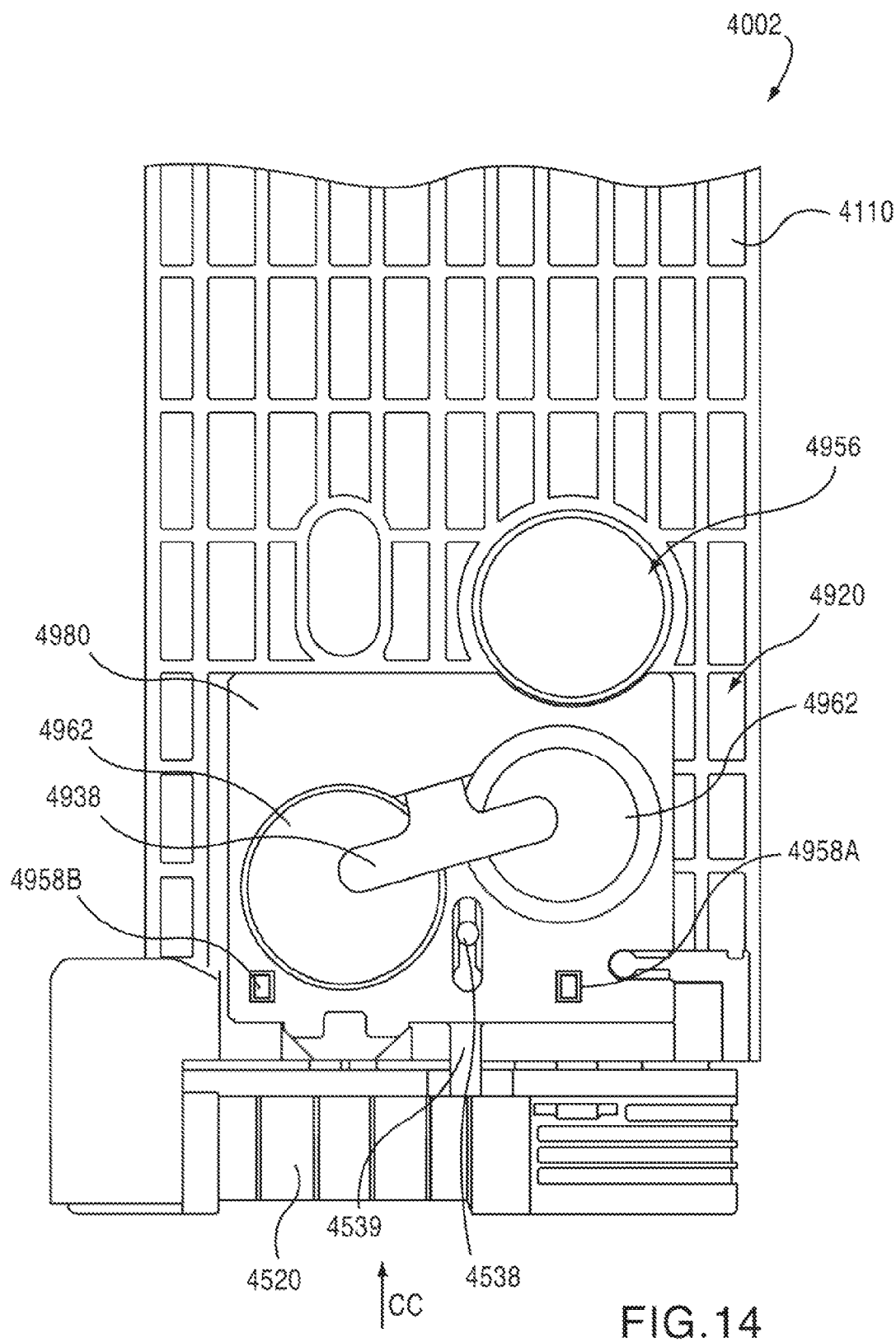
FIG. 14 is a perspective view of a portion of the auto-injector illustrated in FIG. 5 in a fourth configuration.

After the auto-injector 4002 is enabled and placed against the body of the patient, the auto-injector 4002 is actuated by moving the base 4520 proximally towards the housing 4110, as illustrated by arrow CC in FIG. 14. The base 4520 includes an actuator 4538 that actuates the electronic circuit 4920 to trigger a predetermined output or sequence of outputs when the base 4520 is moved from a first position to a second position, as shown in FIG. 13. The actuator 4538 includes a protrusion 4539 that is received within a second opening 4928B (see FIG. 10) defined by the substrate 4924 when the base 4520 is in the first position. The configuration and operation of the protrusion 4539, the second opening 4928B and the second switch 4972B are similar to the configuration and operation of the protrusion 4730, the first opening 4928A and the first switch 4972A, and are therefore not described in detail.

When the actuator 4538 actuates the electronic circuit system 4920, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The processor can also simultaneously output an electronic signal to the first LED 4958A, thereby causing the first LED 4958A to stop flashing, change color or the like, to provide a visual indication that the injection is complete.

Figure 17:
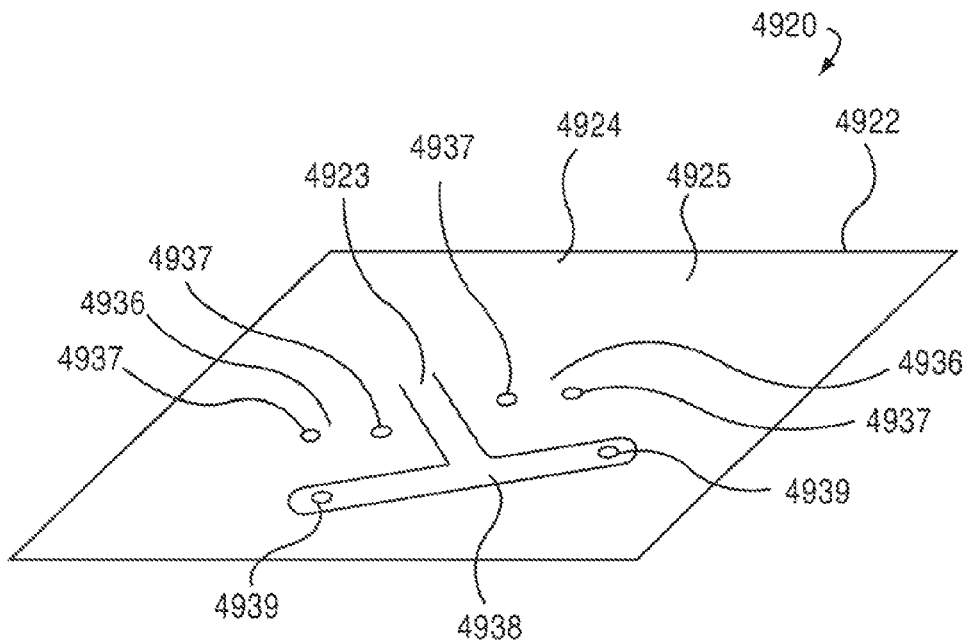
FIGS. 17 through 20 are perspective views of a portion of the auto-injector illustrated in FIG. 10, in a first configuration, a second configuration, a third configuration and a fourth configuration, respectively.

As described above, the batteries 4962 are positioned such that the first electrical contact portions 4936 of the printed circuit board 4922 can be placed in contact with the first surface 4964 of each battery 4962 and the second electrical contact portion 4938 of the printed circuit board 4922 can be placed in contact with the second surface 4966 of each battery 4962. As shown in FIGS. 10 and 17, the first electrical contact portions 4936 each include a pair of electrical contacts 4937 that are operatively coupled to the electronic circuit system 4920. Similarly, the second electrical contact portion 4938 includes a pair of electrical contacts 4939 that is operatively coupled to the electronic circuit system 4920.

Figure 21:
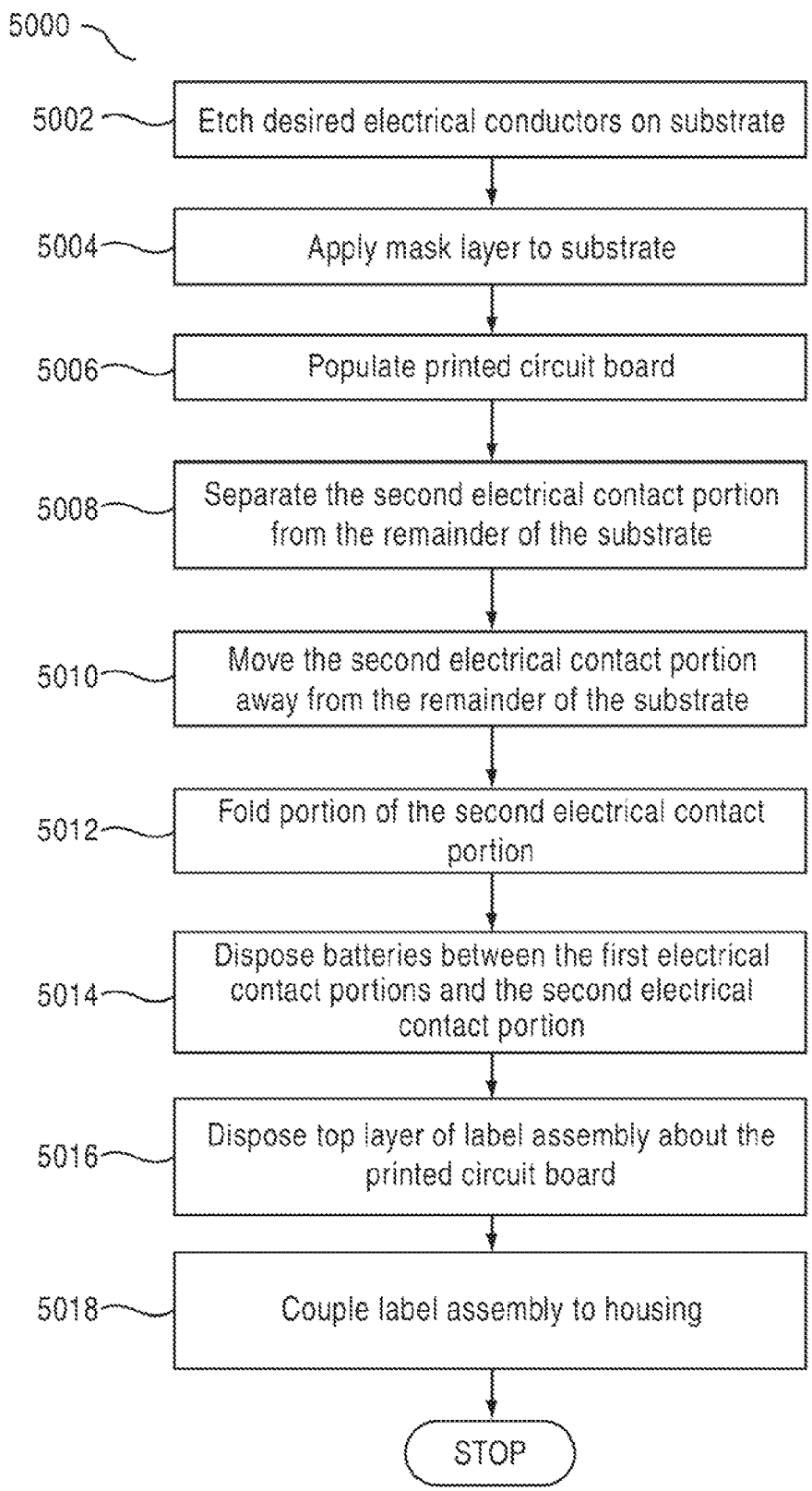
FIG. 21 is a flow chart of a method according to an embodiment of the invention.

The first electrical contact portions 4936 and the second electrical contact portion 4938 are monolithically constructed from the printed circuit board 4922. FIGS. 17-20 are perspective views showing the printed circuit board 4922 in various stages of manufacture. FIG. 21 is a flow chart illustrating a method 5000 for manufacturing a flexible printed circuit board according to an embodiment of the invention. The illustrated method includes disposing a copper layer on the top surface 4925 of the flexible substrate 4924 and etching the desired series of electrical conductors (not shown in FIGS. 17-20) at 5002. A mask layer (not shown) is disposed on portions of the top layer 4925 of the substrate 4924 to electrically isolate selected portions of the electrical conductors from adjacent components at 5004. During this operation, the electrical contacts 4937, 4939 are constructed.

The printed circuit board 4922 is then populated with the microprocessor, switches, output devices and/or other electronic components to form the electronic circuit system 4920 at 5006. For clarity, the circuit components are not shown in FIGS. 17-20. After the printed circuit board 4922 is populated, the portion of the flexible substrate 4924 forming the second electrical contact portion 4938 is separated from the remainder of the substrate 4924 at 5008. As shown in FIG. 17, during this operation, a portion 4923 of the boundary between the second electrical contact portion 4938 and the remainder of the substrate 4924 is left intact.

Figure 18:
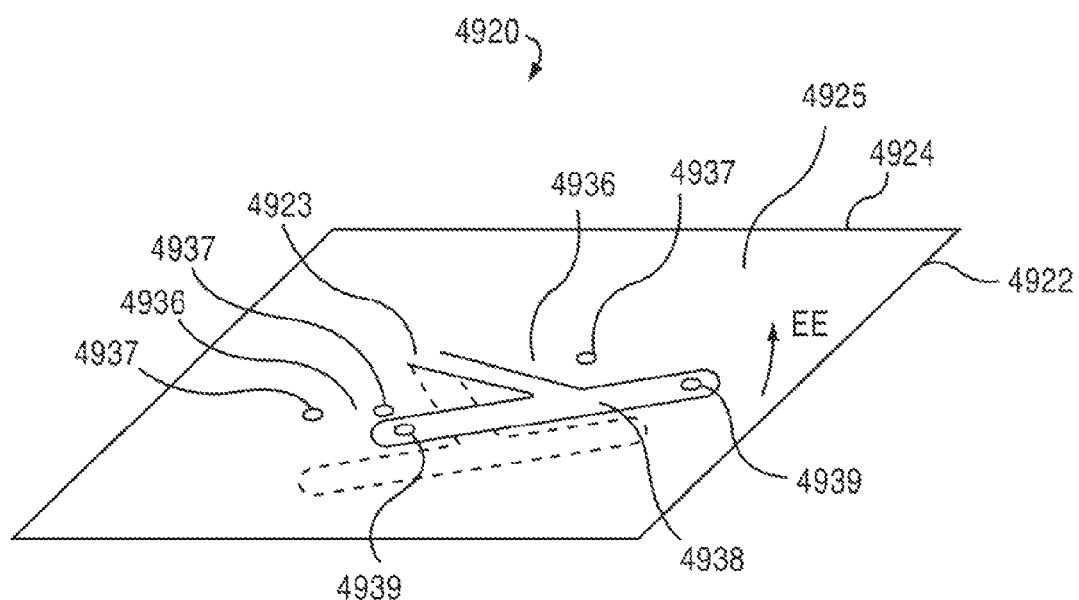
Figure 19:
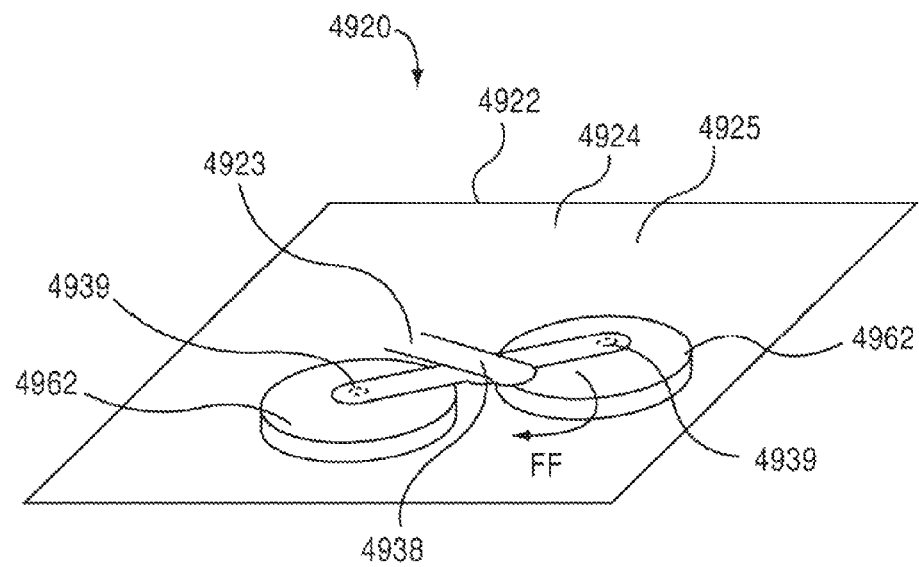
Figure 20:
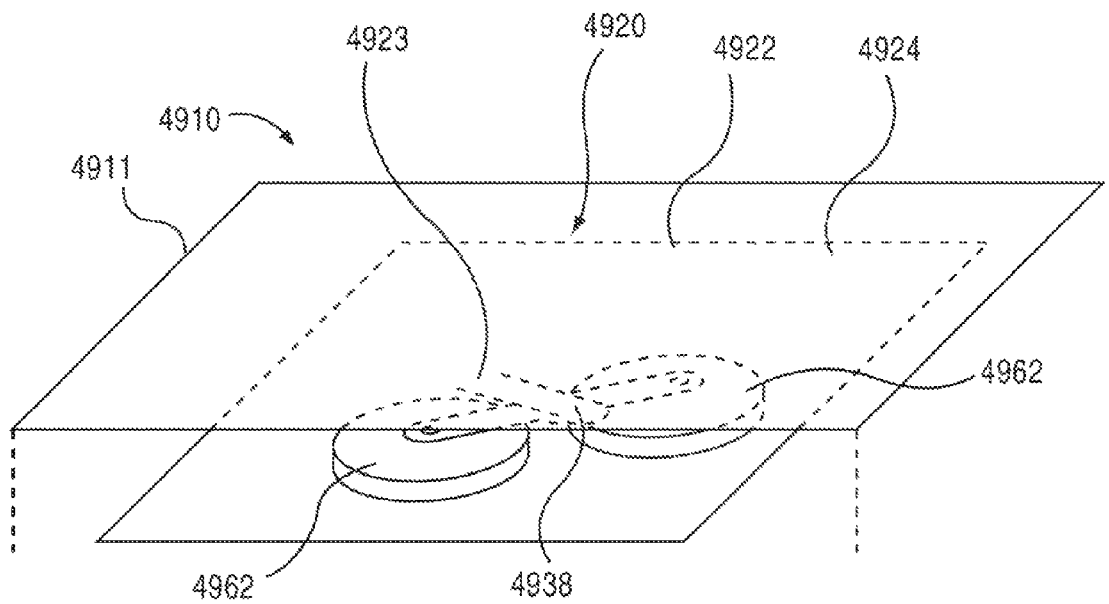

As shown by the arrow EE in FIG. 18, the second electrical contact portion 4938 is then moved upwardly away from the remainder of the substrate 4924 at 5010. In this manner, the second electrical contact portion 4938 is spaced apart from the first electrical contact portions 4936. As shown by the arrow FF in FIG. 19, the portion of the second electrical contact portion 4938 containing the electrical contacts 4939 is then folded so that the electrical contacts 4939 on the second electrical contact portion 4938 are facing the electrical contacts 4937 on the first electrical contact portions 4936, at 5012. In this manner, opposing electrical contacts 4937, 4939 are constructed on the printed circuit board 4922 without disposing electrical conductors on and/or etching multiple surfaces of the printed circuit board 4922.

The batteries 4962 are then disposed between the first electrical contact portions 4936 and the second electrical contact portion 4938 at 5014. Although not shown in FIG. 19, in some embodiments, a battery isolation tab of the type discussed above can be disposed between one of the batteries and the printed circuit board 4922. Once the batteries 4962 are in place, the top layer 4911 of the label 4910 is disposed about the printed circuit board 4922 (see FIG. 20) to maintain the position of the batteries 4962 within the printed circuit board 4922, at 5016. The label assembly 4910 is then coupled to the outer surface of the housing (not shown) at 5018. The label 4910 is coupled to the housing with sufficient tension and/or stretch to maintain the electrical contacts 4937 in electrical communication with the first surface 4964 of each battery 4962 and to maintain the electrical contacts 4939 in electrical communication with the second surface 4966 of each battery 4962. In this manner, the batteries 4962 can be held in place in a printed circuit board 4922 devoid of springs, clips or other rigid members.

As described above, the audio output device 4956, can include, for example, a micro-speaker. In some embodiments, for example, the audio output device 4956 can include an RS-1511A micro-speaker manufactured by Regal Electronics, Inc.

Similarly, the microprocessor 4950 can be a commercially-available processing device dedicated to performing one or more specific tasks. For example, in some embodiments, the microprocessor 4950 can be a commercially-available microprocessor, such as the Sonix SNC 12060 voice synthesizer. Alternatively, the microprocessor 4950 can be an application-specific integrated circuit (ASIC) or a combination of ASICs, which are designed to perform one or more specific functions. In yet other embodiments, the microprocessor 4950 can be an analog or digital circuit, or a combination of multiple circuits.

The microprocessor 4950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the microprocessor 4950, for example, electronically-programmable read only memory (EPROM), erasable electronically-programmable read only memory (EEPROM), or flash memory.

Figure 22:
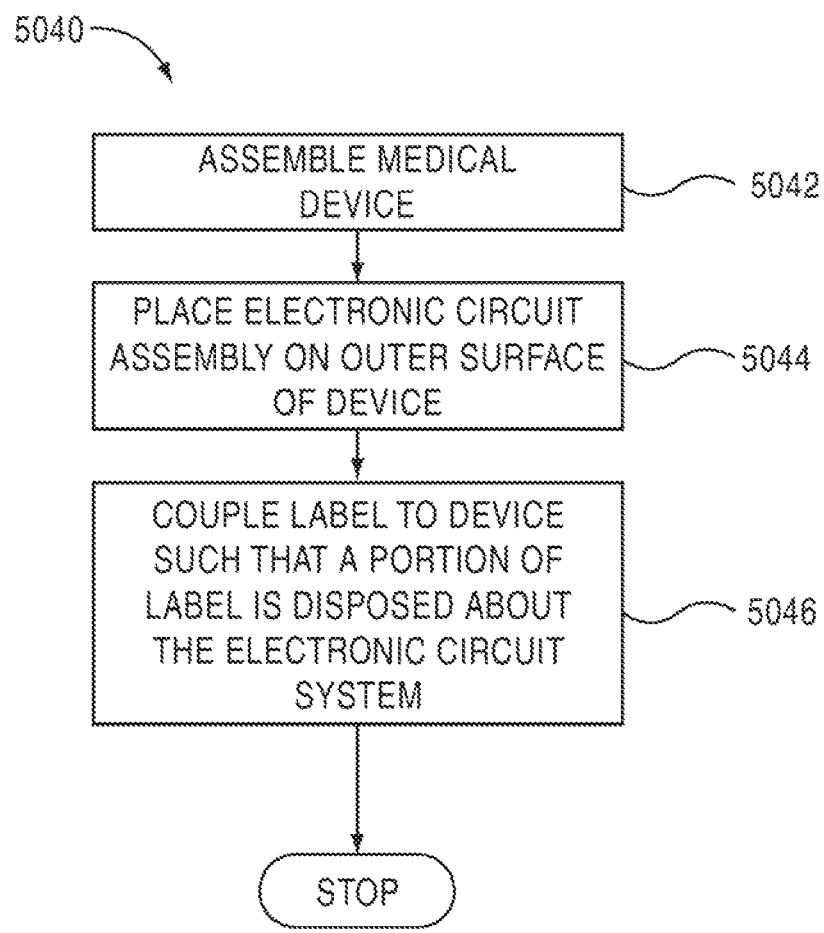
FIG. 22 is a flow chart of a method according to an embodiment of the invention.

FIG. 22 is a flow chart illustrating a method 5040 for manufacturing a medical device according to an embodiment of the invention. The medical device can be any medicament delivery device of the type discussed above, such as, for example, an auto-injector, a pen injector, an inhaler, or a transdermal delivery device. The medical device can also be a medicament container, such as, for example, a pill bottle, a blister pack an intravenous solution bag or the like. The illustrated method includes assembling the medical device, 5042. After the medical device is assembled, an electronic circuit system is placed on an outer surface of the medicament delivery device, 5044. The electronic circuit system can by any electronic circuit system of the type shown and described above. In some embodiments, the electronic circuit system is placed on the outer surface of the medical device in a predetermined orientation. For example, in some embodiments, the electronic circuit system can include openings, such as openings 4928 that are aligned with mating portions of the medical device, such as, for example, protrusions 4730, 4538. In other embodiments, however, the electronic circuit system can be placed on the outer surface of the medical device in any orientation.

After the electronic circuit system is placed on an outer surface of the medical device, a label is coupled to the medical device, 5046. The label, which can be, for example, a label containing a textual indicia, is coupled to the medical device such that a portion of the label is disposed about the electronic circuit system. In this manner, the coupling of the label to the medical device also serves to maintain the electronic circuit system in its position against the outer surface of the medicament delivery device.

Figure 23:
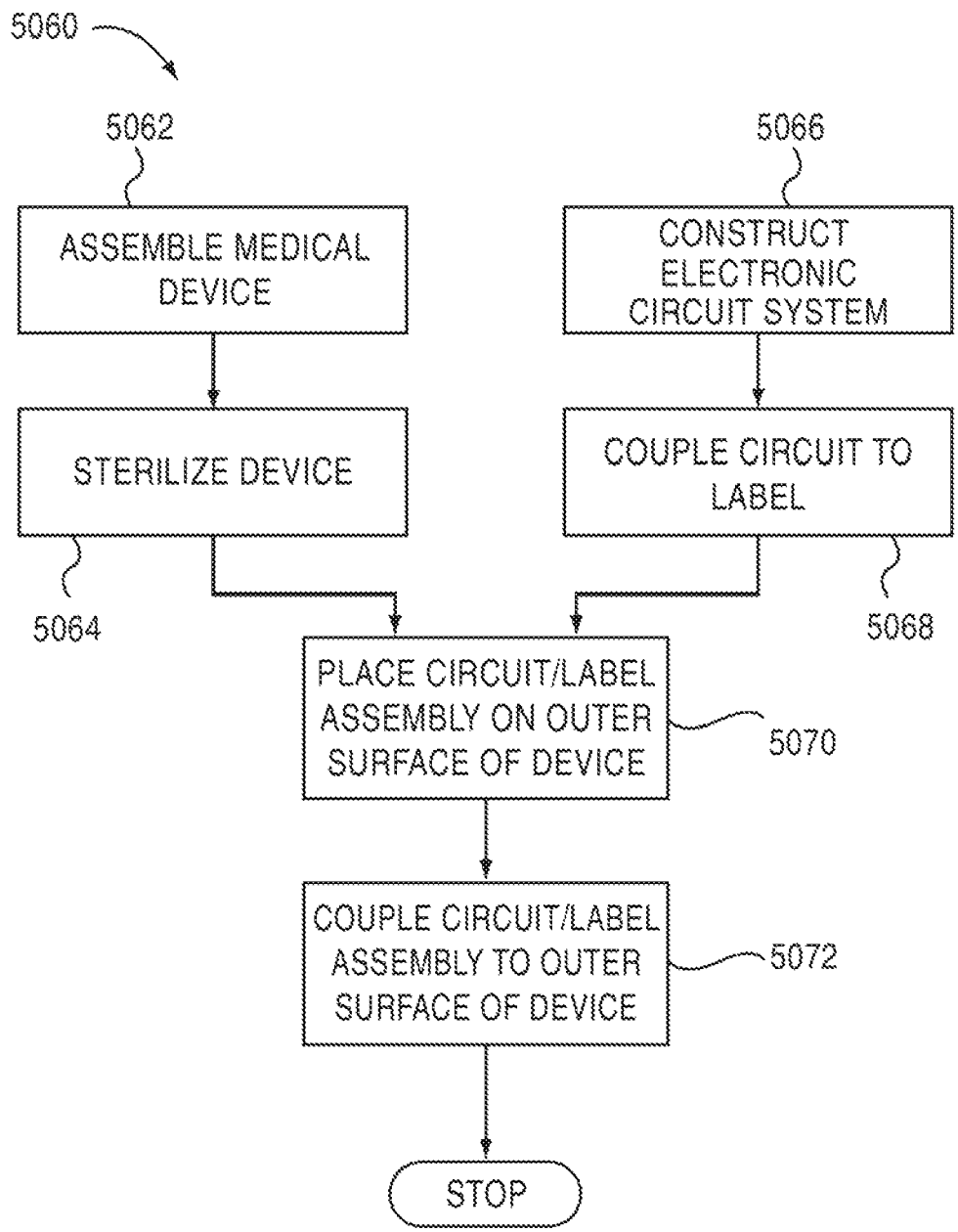
FIG. 23 is a flow chart of a method according to an embodiment of the invention.

FIG. 23 is a flow chart illustrating a method 5060 for manufacturing a medical device according to an embodiment of the invention. The medical device can be any medicament delivery device of the type discussed above, such as, for example, an auto-injector, a pen injector, an inhaler, or a transdermal delivery device. The medical device can also be a medicament container, such as, for example, a pill bottle, a blister pack, an intravenous (IV) bag or the like. The illustrated method includes assembling the medical device, 5062. The medical device is then sterilized using any suitable sterilization process, 5064. In some embodiments, for example, such as those embodiments in which the medicament is epinephrine, the medical device can be sterilized by exposure to ethylene oxide (EtO) gas. In other embodiments, the medical device can be sterilized by exposure to gamma radiation. In yet other embodiments, the medical device can be sterilized by exposure to heat, such as for example, by placing the medicament delivery device into an autoclave.

In parallel with the manufacture of the medical device, the illustrated method includes constructing an electronic circuit system of the type shown and described above, 5066. The electronic circuit system is then coupled to a label, 5068, to form a label assembly. Because the circuit construction is done apart from the manufacture of the medicament delivery device, it is not subjected the sterilization process, which, in some instances, may damage the circuit components.

The illustrated method then includes placing the label assembly on the outer surface of the medical device, 5070. The label assembly is then coupled to the outer surface of the medical device, 5072. In some embodiments, the label assembly can be coupled to the medicament delivery device by an adhesive, an elastic fastener, a shrink wrap or any other suitable method.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the first surface 4912 of the top layer 4911 of the label 4910 is shown and described as being opposite the second surface 4914 of the top layer 4911 of the label 4910, in other embodiments, the first surface 4912 and the second surface 4914 can be adjacent each other and/or co-planar. Similarly, although the top layer 4911 of the label 4910 is shown and described as covering substantially all of the housing 4110, in some embodiments, the top layer 4911 of the label 4910 can cover only a portion of the housing.

Although the label 4910 is shown and described as including a top layer 4911, an intermediate layer 4980 and a printed circuit board 4922, in some embodiments, the layers comprising the label 4910 can be arranged in any suitable order. For example, in some embodiments, a multi-layered label can include a printed circuit board as an intermediate layer. In other embodiments, a multi-layered label can include a printed circuit board as the outer layer. Moreover, in yet other embodiments, the label need not include multiple layers. For example, in some embodiments, a label can include a single layer that includes an electronic circuit system and textual indicia.

Although the indicia 4916 are shown and described as being visible (e.g., textual indicia and/or symbolic indicia), in some embodiments, a label can include indicia that are haptic. For example, in some embodiments a label can include Braille. In other embodiments, a label can include indicia having a distinct feel, such as for example, a particularly rough or smooth surface.

Although the electronic circuit system 4920 is shown and described as including a printed circuit board 4922 having a flexible substrate 4924, in other embodiments, an electronic circuit system can include a rigid printed circuit board. In yet other embodiments, an electronic circuit system can include a printed circuit board having a substrate having at least a rigid portion.

Moreover, in some embodiments, an electronic circuit system need not include a printed circuit board. For example, in some embodiments, an electronic circuit system can include electronic components operatively coupled by any suitable method other than by a printed circuit board.

Similarly, although the components included in the electronic circuit system 4920 (e.g., the microprocessor 4950, the LEDs 4958A and 4958B or the like) are shown and described as being operatively coupled by electrical conductors 4934, in other embodiments, the components can be operatively coupled without being physically connected. For example, in some embodiments, at least a portion of the components included in an electronic circuit system can be inductively coupled. In other embodiments, at least a portion of the components included in an electronic circuit system can be evanescently coupled.

Although the switches 4972A and 4972B are shown and described as being "tear-through" switches that are monolithically formed from the electrical conductors 4934, in other embodiments, a switch can be formed separately from the electrical conductors 4934. For example, in some embodiments, an electrical circuit system can include a series of first electrical conductors having a first set of characteristics (e.g., the width, height, material from which the conductor is fabricated or the like) and a switch constructed from a second electrical conductor having a second set of characteristics different than the first set of characteristics. In other embodiments, a switch can be a separate component, such as, for example, a microswitch, that is mounted to the printed circuit board. In yet other embodiments, an electrical circuit system can include a "pop-out" switch that includes a biasing member to bias the switch in a predetermined state. In yet other embodiments, an electrical circuit system can include a switch that is disposed at a location other than on a printed circuit board.

Similarly, although the switches 4972A and 4972B are shown and described as being irreversibly movable from a first state to a second state, in other embodiments, a switch can be reversibly movable between a first state and a second state. Moreover, in yet other embodiments, a switch can have more than two distinct states.

Although the actuators 4732, 4539 are shown and described as being configured to move in a direction substantially parallel to the surface of the substrate 4924, in other embodiments, an actuator can be configured to actuate an electronic circuit system by moving in any direction. For example, in some embodiments a circuit actuator can be moved in a direction substantially normal to a portion of an electronic circuit system.

Similarly, although the actuators 4732, 4539 are shown and described as actuating the switches 4972A and 4972B by tearing and/or deforming a portion of the substrate 4924, in other embodiments, a switch can be moved from a first state to a second state without deforming the substrate. For example, in some embodiments, an electronic circuit system can include a printed circuit board having a substrate and a frangible switch tab disposed on the substrate. An electrical conductor and/or a switch can be disposed on the frangible switch tab, such that when the switch tab is removed from the substrate the switch is moved from a first state to a second state. In this manner, the switch can be actuated without tearing and/or deforming a portion of the substrate.

Although the actuators 4732, 4539 are shown and described as being included on the safety lock 4710 and the base 4520, respectively, in other embodiments, the actuators can be included on any component of a medicament delivery device. For example, in some embodiments, an auto-injector can include a start button having an actuator configured to actuate an electronic circuit system. In other embodiments, an auto-injector can include a movable member configured to move a medicament container and/or a needle within a housing of the auto-injector, the movable member including an actuator configured to actuate an electronic circuit system.

Although the safety lock 4710 is shown and described as being removed from the housing 4110 of the auto-injector 4002 when in its second position, in other embodiments, a safety lock can remain coupled to the housing of an auto-injector when in its second position. For example, in some embodiments, a safety lock can be moved from its first position to its second position by rotating a portion of the safety lock.

Certain components of the auto-injector 4002 are shown and described as being coupled together via protrusions and mating openings. The protrusions and/or openings can be disposed on any of the components to be coupled together and need not be limited to only a certain component. For example, the safety lock 4710 is shown and described as including an actuator 4732 having a protrusion 4730 configured to be received within an opening 4928A defined by the substrate 4924. In some embodiments, however, the protrusions can be disposed on the substrate 4924 and the mating openings can be defined by the actuator 4732. In other embodiments, such components can be coupled together in any suitable way, which need not include protrusions and mating openings. For example, in some embodiments, an actuator can be operatively coupled to an actuation portion of a substrate via mating shoulders, clips, adhesive or the like.

Similarly, although certain components of the auto-injector 4002 are shown and described as being constructed from multiple separate components, in some embodiments, such components can be monolithically constructed. For example, the needle guard 4810 and the battery isolation tab 4860 are shown and described as being constructed separately and then coupled together. In other embodiments, a needle guard and a battery isolation tab can be constructed monolithically.

Although the electronic circuit systems are shown and described above as being configured to output primarily audible and visual outputs, in other embodiments, an electronic circuit system can be configured to produce any suitable output. For example, in some embodiments, an electronic circuit system can produce a haptic output, such as a vibratory output produced by a piezo-electric actuator. In other embodiments, an electronic circuit system can produce a thermal output, produced by a heating or cooling element.

Similarly, the visual output devices shown and described above can include any suitable type of visual output device, such as, for example, a liquid crystal display, an organic polymer display, a fiber optic display. In this manner, the visual output produced by an electronic circuit system can include text messages, numerical indications of the dosage or the like.

Although the electronic circuit systems are shown and described above as outputting recorded speech in English, in other embodiments, the electronic circuit system can output recorded speech in any language. In yet other embodiments, the electronic circuit system can output recorded speech in multiple languages.

Although the electronic circuit systems are shown and described above as including a proximity sensor, in other embodiments, an electronic circuit system can include any suitable sensor for providing feedback to the electronic circuit system. For example, in some embodiments, the electronic circuit system can include a pressure sensor configured to sense the internal gas pressure within a gas-powered auto-injector. In this manner, the electronic circuit system can output an instruction and/or a status message when the internal gas pressure crosses a predetermined threshold. For example, in some embodiments, when the internal gas pressure rapidly increases, the electronic circuit system can output a message, such as, for example, "Internal gas chamber has been successfully punctured—injection is in process."

Similarly, in some embodiments, the electronic circuit system can include a temperature sensor configured to sense the temperature of the medicament contained within the medicament delivery device. In this manner, the electronic circuit system can output an instruction and/or a status message when the medicament is too cold for effective delivery. For example, in some embodiments, when the medicament is too cold for effective delivery (this may occur, for example, if the medicament delivery device has been left outside overnight), the electronic circuit system can output a message, such as, for example, "Medicament is too cold—please briskly rub the auto-injector between your hands."

Although the batteries 4962 are shown and described as having a first surface 4964 (an electrically negative terminal) and a second surface 4966 (an electrically positive terminal) opposite the first surface, in other embodiments the batteries can include a first surface and a second surface that are adjacent each other and/or co-planar. In other embodiments, an electronic circuit system can be powered by a battery having any shape and/or any number of surfaces. In yet other embodiments, an electronic circuit system can be powered by any suitable energy storage device, such as, for example, a capacitor, solar cell, spring actuated generator, or the like.

Although the medicament delivery devices have been shown and described above as being primarily single-use medical injectors, in some embodiments a medicament delivery device can include any suitable device for delivering one or more doses of a medicament into a patient's body. For example, in some embodiments, a medicament delivery device can be a pen injector containing multiple doses of a chronic-care medicament, such as, for example, insulin. In such embodiments, an electronic circuit system can output instructions associated with not only an initial use of the medicament delivery device, but also associated with repeated uses, dosage monitoring or the like. In other embodiments, a medicament delivery device can include a transdermal medicament delivery device, an inhaler or a nasal medicament delivery device.

Figure 24:
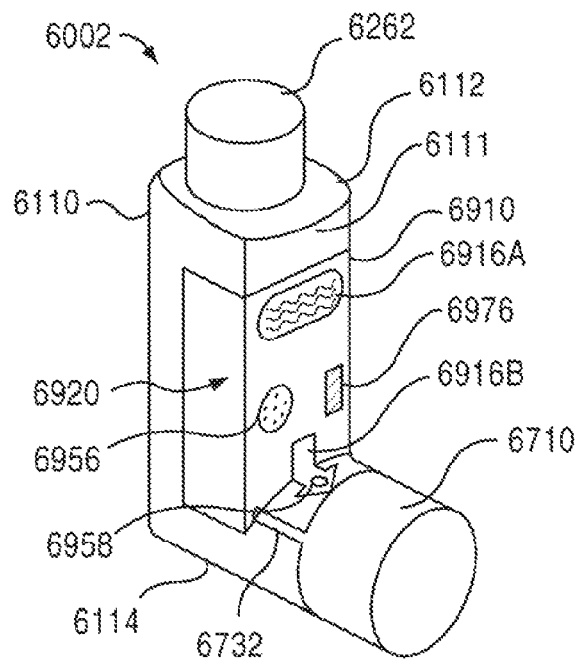
FIGS. 24 and 25 are perspective views of a medicament delivery device according to an embodiment of the invention.
Figure 25:
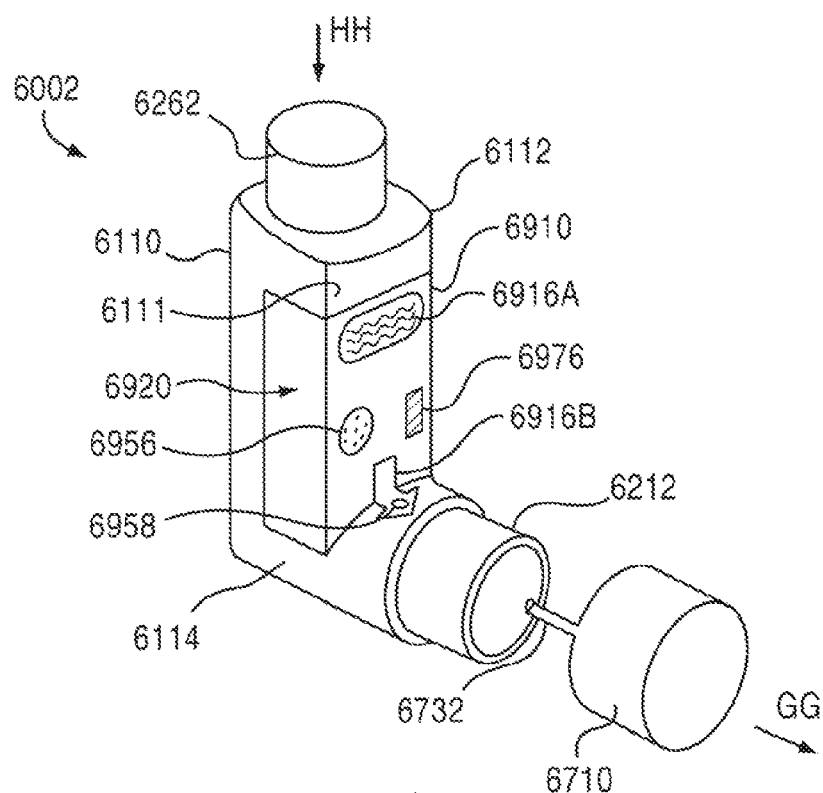

FIGS. 24 and 25 show an inhaler 6002 according to an embodiment of the invention. The inhaler 6002 includes a housing 6110 and a medicament container 6262 movably disposed within the housing 6110. The medicament container 6262 includes a metering mechanism (not shown in FIGS. 24 and 25) configured to discharge a predetermined volume of medicament when the inhaler 6002 is actuated.

The housing 6110 has a proximal end portion 6112 and a distal end portion 6114. An label 6910, which includes at least a portion of an electronic circuit system 6920, is disposed on an outer surface 6111 of the housing 6110. As described above, a portion of the label 6910 can include a textual indicia 6916. Similar to the electronic circuit systems shown and described above, the electronic circuit system 6920 is configured to output at least one electronic signal associated with the user of the inhaler 6002. The electronic circuit system 6920 includes a microprocessor (not shown), a microspeaker 6956 and an LED 6958. The electronic circuit system 6920 also includes a motion sensor 6976, the function of which is discussed in more detail below.

The distal end portion 6114 of the housing 6110 includes a mouthpiece 6212 about which a protective cap 6710 is disposed. Prior to use, the inhaler 6002 is first enabled by removing the protective cap 6710, as shown by the arrow GG in FIG. 25. The protective cap 6710 includes an actuator 6732 that actuates the electronic circuit system 6920 to trigger a predetermined output or sequence of outputs when the protective cap 6710 is removed. In some embodiments, the actuator 6732 can include a protrusion that is received by an actuation portion of the electronic circuit system 6920, in a similar manner as described above. In other embodiments, the actuator 6732 can be configured to engage a microswitch that can be repeatedly moved between a first state and a second state.

When actuated, the electronic circuit system 6920 can output one or more predetermined electronic outputs. For example, in some embodiments, the electronic circuit system 6920 can output an audible message via the microspeaker 6956 instructing the user to "vigorously shake the inhaler for five seconds." The processor can simultaneously enable the motion sensor 6976.

Upon receiving a predetermined input from the motion sensor 6976, which can be any sensor suitable for detecting the rapid motion of the inhaler 6002, the processor can then send an electronic signal to produce a second audible message. Such a message can state, for example, "the inhaler is now sufficiently shaken and is ready for use." In some embodiments, the electronic circuit system 6920 can also output an instruction associated with the correct placement of the inhaler 6002. For example, the electronic circuit system 6920 can output an audible message stating "please place the mouthpiece in your mouth and firmly press down on the medicament container." The electronic circuit system 6920 can also simultaneously output a signal to the LED 6958 to provide a visual indication of where the mouthpiece 6212 is located.

After the inhaler 6002 is enabled and placed within the mouth of the patient, the inhaler 6002 is actuated by moving the medicament container 6262 distally within housing 6110, as illustrated by arrow HH in FIG. 25. In some embodiments, the medicament container 6262 can include an actuator (not shown) that actuates the electronic circuit 6920, in a manner similar to those described above, to trigger a predetermined output or sequence of outputs. For example, in some embodiments, the processor can output an electronic signal associated with recorded speech to the microspeaker 6956. Such an electronic signal can be, for example, associated with a recorded message notifying the user that the injection is complete, instructing the user on post-injection procedures, instructing the user on post-injection medical treatment or the like. Such a status message can state, for example, "The injection is now complete."

In other embodiments, a medicament delivery device can include a transdermal medicament delivery device, such as for example, a medicament patch. In such embodiments, an electronic circuit system can be configured, for example, to output instructions associated with the enablement, placement and/or removal of the transdermal medicament delivery device. For example, in some embodiments, the electronic circuit system can be actuated by removing a protective barrier that seals the portion of the device that contacts the skin.

Although the medical devices are shown and described above as being medicament delivery devices, such as, for example, medical injectors, inhalers or the like, in other embodiments, a medical device can include a medicament container, such as, for example, a pill bottle, a blister pack or the like.

Although various embodiments have been described as having particular features and/or combinations of components, other embodiments are possible having a combination of any features and/or components from any of embodiments where appropriate.

What is claimed is:

1. An apparatus, comprising:
a housing associated with a medical device;
a container disposed within the housing;
a movable member having a first end portion and a second end portion, the second end portion disposed within the container;
a first actuator assembly configured to release an energy storage member disposed within the housing, the first end portion of the movable member configured to receive a force produced by the energy storage member to move the second end portion of the movable member within the container in response to the energy storage member being released;
an electronic circuit system including a first switch, a second switch, and an audible output device, the audible output device coupled to the housing, the electronic circuit system configured to output a first recorded speech output via the audible output device when the first switch is actuated, the electronic circuit system configured to output a second recorded speech output via the audible output device when the second switch is actuated; and
a second actuator assembly coupled to the housing, the second actuator assembly including an outer surface, a first protrusion, and a second protrusion, the outer surface accessible from outside of the housing, the first protrusion of the second actuator assembly being aligned with the first switch and configured to actuate the first switch when a first portion of the outer surface is manipulated, the second protrusion of the second actuator assembly being aligned with the second switch and configured to actuate the second switch when a second portion of the outer surface is manipulated.

2. The apparatus of claim 1, wherein:
the electronic circuit system includes a printed circuit board, the first switch coupled to a first portion of the printed circuit board, the second switch coupled to a second portion of the printed circuit board; and
the first protrusion is configured to contact the first switch to actuate the first switch, the second protrusion is configured to contact the second switch to actuate the second switch.

3. The apparatus of claim 1, wherein the first portion of the outer surface is accessible from outside of the housing and is configured to be manipulated separately from the second portion of the outer surface such that the first protrusion contacts the first switch to actuate the first switch when the first portion of the outer surface is moved relative to the housing.

4. The apparatus of claim 1, wherein the energy storage member is a non-electronic energy storage member.

5. The apparatus of claim 1, wherein the electronic circuit system is configured to produce a predetermined sequence of electronic outputs, the sequence including the first recorded speech output.

6. The apparatus of claim 1, wherein the electronic circuit system is configured to output the first recorded speech output for a predetermined time period, the electronic circuit system is configured to produce, in response to actuation of the first switch, a third recorded speech output after the predetermined time period has elapsed, the third recorded speech output different from the first recorded speech output.

7. The apparatus of claim 1, wherein:
the medical device is an autoinjector; and
at least one of the first recorded speech output or the second recorded speech output is associated with an injection event with the autoinjector.

8. The apparatus of claim 1, wherein:
the container is configured to move within the housing in response to the energy storage member being actuated.

9. The apparatus of claim 1, wherein the force is a first force, the second end portion of the movable member is configured to move in a first direction within the container in response to the energy storage member being actuated, the apparatus further comprising:
a retraction member configured to transmit a second force to move the movable member in a second direction within the container, the second direction opposite the first direction.

10. The apparatus of claim 1, wherein the container contains a medicament, the second end portion of the movable member configured to expel at least a portion of the medicament from the container when the second end portion of the movable member is moved within the container.

11. An apparatus comprising:
an outer housing associated with a medical injector;
an inner housing disposed within the outer housing;
an energy storage member disposed within the outer housing, the energy storage member configured to produce a force;

a movable member having a first end portion and a second end portion, the first end portion configured to receive the force produced by the energy storage member to move the second end portion of the movable member within the inner housing;

an electronic circuit system including a first switch, a second switch and an audible output device, the audible output device coupled to the outer housing, the electronic circuit system configured to produce a first recorded speech output via the audible output device when the first switch is actuated, the electronic circuit system configured to produce a second recorded speech output via the audible output device when the second switch is actuated, the second recorded speech output different from the first recorded speech output; and an actuator assembly coupled to the outer housing, the actuator assembly including an outer surface and an inner surface, the inner surface including a first protrusion aligned with the first switch, the first protrusion configured to move relative to the outer housing when the outer surface is manipulated to actuate the first switch, the inner surface including a second protrusion aligned with the second switch, the second protrusion configured to move relative to the outer housing when the outer surface is manipulated to actuate the second switch.

12. The apparatus of claim 11, wherein the second end portion of the movable member is configured to move from a first position to a second position within inner housing, the movable member and the inner housing being collectively configured to limit a distance between the first position and the second position.

13. The apparatus of claim 11, wherein:
the inner housing is configured to move within the outer housing in response to the force being received by the first end portion of the movable member.

14. The apparatus of claim 11, wherein the force is a first force, the second end portion of the movable member is configured to move in a first direction within the inner housing in response to the first force being received by the first end portion of the movable member, the apparatus further comprising:
a retraction member configured to transmit a second force to move the movable member in a second direction within the inner housing, the second direction opposite the first direction.

15. The apparatus of claim 11, wherein:
the electronic circuit system includes a printed circuit board, the first switch coupled to a first portion of the printed circuit board, the second switch coupled to a second portion of the printed circuit board; and
the first protrusion is configured to contact the first switch to actuate the first switch, the second protrusion is configured to contact the second switch to actuate the second switch.

16. The apparatus of claim 11, wherein the outer housing defines an opening within which the audible output device is disposed.

17. The apparatus of claim 11, wherein the energy storage member is a non-electronic energy storage member.

18. The apparatus of claim 11, wherein the electronic circuit system is configured to produce a third recorded speech output a predetermined time period after actuation of the first switch.

19. The apparatus of claim 11, wherein the a first portion of the outer surface is configured to be manipulated separately from a second portion of the outer surface, the first protrusion configured to contact the first switch when the first portion of the outer surface is manipulated, the second protrusion configured to contact the second switch when the second portion of the outer surface is manipulated.

20. The apparatus of claim 11, wherein:
the electronic circuit system is configured to produce the first recorded speech output for a predetermined time period; and
the electronic circuit system is configured to produce, in response to actuation of the first switch, a third recorded speech output after the predetermined time period has elapsed, the third recorded speech output different from the first recorded speech output.

21. The apparatus of claim 11, wherein the electronic circuit system is configured to produce at least one of the first recorded speech output or the second recorded speech output in a plurality of different languages.

22. The apparatus of claim 11, wherein the first protrusion is spaced apart from the second protrusion.

23. The apparatus of claim 11, wherein:
the electronic circuit system includes a printed circuit board, the first switch coupled to a first portion of the printed circuit board, the second switch coupled to a second portion of the printed circuit board, the second portion spaced apart from the first portion;
the first protrusion is configured to contact the first switch to actuate the first switch when the first protrusion is moved relative to the first housing, the second protrusion is configured to contact the second switch to actuate the second switch when the second protrusion is moved relative to the first housing; and
the audible output device is a speaker retained within an opening defined by the outer housing by a cover member, the cover member defining a plurality of sound openings.

24. An apparatus comprising:
a housing associated with an automatic injection device;
a movable member having a first end portion and a second end portion;
a non-electronic energy storage member disposed within the housing, the energy storage member configured to exert a force on the first end portion of the movable member to move the second end portion of the movable member within the housing;
an electronic circuit system including a printed circuit board, a first switch, a second switch, and an audible output device, the first switch coupled to a first portion of the printed circuit board, the second switch coupled to a second portion of the printed circuit board, the electronic circuit system coupled within the housing, the electronic circuit system configured to produce a first recorded speech output via the audible output device when the first switch is actuated, the electronic circuit system configured to produce a second recorded speech output via the audible output device when the second switch is actuated; and
an actuator assembly coupled to the housing, the actuator assembly including an outer surface and an inner surface, the inner surface including a first protrusion configured to move relative to the housing to actuate the first switch when a first portion of the outer surface is manipulated, the inner surface including a second protrusion configured to move relative to the housing to actuate the second switch when a second portion of the outer surface is manipulated.

25. The apparatus of claim 24, further comprising:
a cover configured to be coupled to the housing to retain the audible output device within an opening defined by the housing.

26. The apparatus of claim 24, wherein the housing iris an outer housing, the apparatus further comprising:
an inner housing disposed within the outer housing, the inner housing defining a passageway therein,
the second end portion of the movable member is configured to move from a first position to a second position within the passageway when the force is exerted on the first end portion of the movable member, the movable member and the inner housing being collectively configured to limit a distance between the first position and the second position.

27. The apparatus of claim 24, wherein the electronic circuit system is configured to produce a predetermined sequence of electronic outputs, the sequence including the first recorded speech output.

28. The apparatus of claim 24, wherein the electronic circuit system is configured to output the first recorded speech output for a predetermined time period, the electronic circuit system is configured to produce, in response to actuation of the first switch, a third recorded speech output after the predetermined time period has elapsed, the third recorded speech output different from the first recorded speech output.

29. The apparatus of claim 24, wherein first the recorded speech output is associated with an injection event associated with the automatic injection device.

30. The apparatus of claim 26, wherein the first portion of the outer surface is configured to be manipulated separately from the second portion of the outer surface, the first protrusion configured to contact the first switch when the first portion of the outer surface is manipulated, the second protrusion configured to contact the second switch when the second portion of the outer surface is manipulated.

31. The apparatus of claim 24, wherein:
the first protrusion is aligned with the first switch
the second protrusion is spaced apart from the first protrusion and is aligned with the second switch;
the audible output device is a speaker retained within an opening defined by the outer housing by a cover member, the cover member defining a plurality of sound openings.

* * * * *